United States Patent
Sahi et al.

(10) Patent No.: US 12,256,762 B2
(45) Date of Patent: *Mar. 25, 2025

(54) SWEETENER COMPOSITION AND METHODS OF MAKING IT

(71) Applicant: eBIO Nutritional Sciences LLC, Danville, VA (US)

(72) Inventors: Carl R. Sahi, Coventry, CT (US); John M. Polidoro, Tolland, CT (US); Mark Ennis Ketner, Fuquay Varina, NC (US); Dakshinamurthy Devanga Chinta, Morrisville, NC (US)

(73) Assignee: eBIO Nutritional Sciences LLC, Danville, VA (US)

( * ) Notice: Subject to any disclaimer, the term of this patent is extended or adjusted under 35 U.S.C. 154(b) by 460 days.

This patent is subject to a terminal disclaimer.

(21) Appl. No.: 17/689,202

(22) Filed: Mar. 8, 2022

(65) Prior Publication Data

US 2022/0183335 A1 Jun. 16, 2022

Related U.S. Application Data

(63) Continuation of application No. 16/637,443, filed as application No. PCT/US2018/045770 on Aug. 8, 2018, now Pat. No. 11,304,433.

(60) Provisional application No. 62/542,524, filed on Aug. 8, 2017.

(51) Int. Cl.
| | |
|---|---|
| *A23L 27/30* | (2016.01) |
| *A23L 2/60* | (2006.01) |
| *A23L 29/00* | (2016.01) |
| *A61K 47/26* | (2006.01) |

(52) U.S. Cl.
CPC ............... *A23L 27/36* (2016.08); *A23L 2/60* (2013.01); *A23L 29/04* (2016.08); *A61K 47/26* (2013.01)

(58) Field of Classification Search
CPC ............ A23L 27/36; A23L 29/04; A23L 2/60
See application file for complete search history.

(56) References Cited

U.S. PATENT DOCUMENTS

| | | |
|---|---|---|
| 5,556,659 A | 9/1996 | De Pedro et al. |
| 2003/0113307 A1 | 6/2003 | Selzer |
| 2008/0226790 A1 | 9/2008 | Johnson et al. |
| 2010/0239684 A1 | 9/2010 | Fukui |
| 2011/0104329 A1 | 5/2011 | Boghani et al. |
| 2012/0196019 A1 | 8/2012 | Shi et al. |
| 2013/0309362 A1 | 11/2013 | Bromley |
| 2014/0242214 A1 | 8/2014 | Boghani et al. |
| 2015/0086695 A1 | 3/2015 | Oglesby |
| 2016/0198751 A1 | 7/2016 | Fletcher et al. |
| 2016/0235102 A1 | 8/2016 | Oglesby |
| 2016/0316799 A1 | 11/2016 | Aglione et al. |
| 2017/0188606 A1 | 7/2017 | Lancaster et al. |

FOREIGN PATENT DOCUMENTS

| | | |
|---|---|---|
| JP | H01-176443 A | 7/1989 |
| JP | 2001-113157 A | 4/2001 |
| JP | 2007-222084 A | 9/2007 |
| JP | 2011-101637 A | 5/2011 |
| JP | 2017-500050 A | 1/2017 |
| JP | 2020-530311 A | 10/2020 |
| WO | 2008030949 A1 | 3/2008 |
| WO | 2009037274 A1 | 3/2009 |
| WO | 2011/004395 A1 | 1/2011 |
| WO | 2015015209 A1 | 2/2015 |
| WO | 2017066799 A1 | 4/2017 |

OTHER PUBLICATIONS

Saito, et al. "Artificial Sweeteners and Glucose Metabolism: A Review of the Literature Published Since 2000". J Jpn Soc Nutr Food Sci vol. 66, 2013, pp. 69-75 (with English-language abstract.).
European Search Report issued in EP 18 84 3583 dated Jul. 24, 2020; 9 Pages.
Hellfritsch, et al., Human Psychometric And Taste Receptor Responses To Steviol Glycosides, J. Agric. Food Chem., Jul. 11, 2012: 60(27): 6782-6793 (Abstract only) And Written Opinion dated October.
International Patent Application PCT/US2018/045770: International Search Report 22, 2018, 8 pages.

*Primary Examiner* — Jeffrey P Mornhinweg
(74) *Attorney, Agent, or Firm* — Quicker Law, LLC

(57) ABSTRACT

A sweetener composition includes a plurality of assembled particles including natural, non-nutritive sweetener molecules, organic scaffold particles and at least one additive. The natural, non-nutritive sweetener molecules include hydrophilic moieties and hydrophobic moieties. The organic scaffold particles include at least one compositional component including a lipid. The at least one additive includes a surfactant, a stabilizer, an emulsifier, a hydrocolloidal material, a ripening inhibitor, a weighting agent, an excipient, a flavoring agent, a coloring agent, a preservative, a masking agent, a texture enhancer, or a combination thereof. Methods of making the sweetener composition are also described.

19 Claims, 6 Drawing Sheets

SWEETENER COMPOSITION AND METHODS OF MAKING IT

CROSS-REFERENCE TO RELATED APPLICATIONS

This application is a Continuation of U.S. patent application Ser. No. 16/637,443, filed Feb. 7, 2020; which is a National Stage of International Patent Application No. PCT/US2018/045770, filed Aug. 8, 2018; which claims the benefit of U.S. provisional application No. 62/542,524, filed Aug. 8, 2017, the disclosures of all of which are incorporated herein by this reference in their entireties.

FIELD OF THE DISCLOSURE

The present disclosure relates to sweetener compositions, and in particular to sweetener compositions having a commercially desirable flavor profile and that are based on natural, non-nutritive molecules that have an innate flavor profile with commercially undesirable tastes.

BACKGROUND OF THE DISCLOSURE

Many natural, non-nutritive sweetener molecules include a hydrophobic isoprenoid backbone linked to one or more molecules that elicit a sweet taste response. The *stevia* extract Rebaudioside A (Reb A), for example, has a hydrophobic (steviol diterpene) backbone with three glucose molecules on the C-15 end and one glucose molecule on the other end. In many cases the hydrophobic backbone interacts with both the sweet and bitter taste receptors of the oral cavity in such a fashion to elicit a delayed perception of sweetness, and lingering sweet and bitter aftertastes when tasted at concentrations relevant to foods and beverages. It is believed that most sweetener molecules of this type, in an aqueous solution and within the bounds of its free molecular motions, configure themselves to a lowest energy state where the hydrophobic backbone of the molecule orients to minimize its hydrophobic exposure to the aqueous solution, and the hydrophilic sweet molecules remain immersed in the solution. In this configuration, both portions of the molecule are able to interact with sweet and bitter receptors, thereby eliciting an overall undesirable temporal taste profile when consumed. Moreover, in certain situations the hydrophobic regions of both receptors and/or their adjacent tissue may offer a preferential hydrophobic surface for the sweetener molecules to adhere to and prolong receptor activation, resulting in the taste profile taking longer to take affect and making it last longer (i.e., prolonging the bitter and/or sweet aftertaste). Further, the taste profile of these sweetener molecules can be dependent on the beverage or food system in which they are used, making it difficult to optimize sweetener profiles for a particular food/beverage application.

These and other shortcomings are addressed by aspects of the present disclosure.

BRIEF DESCRIPTION OF THE FIGURES

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

SUMMARY

Figure 1:
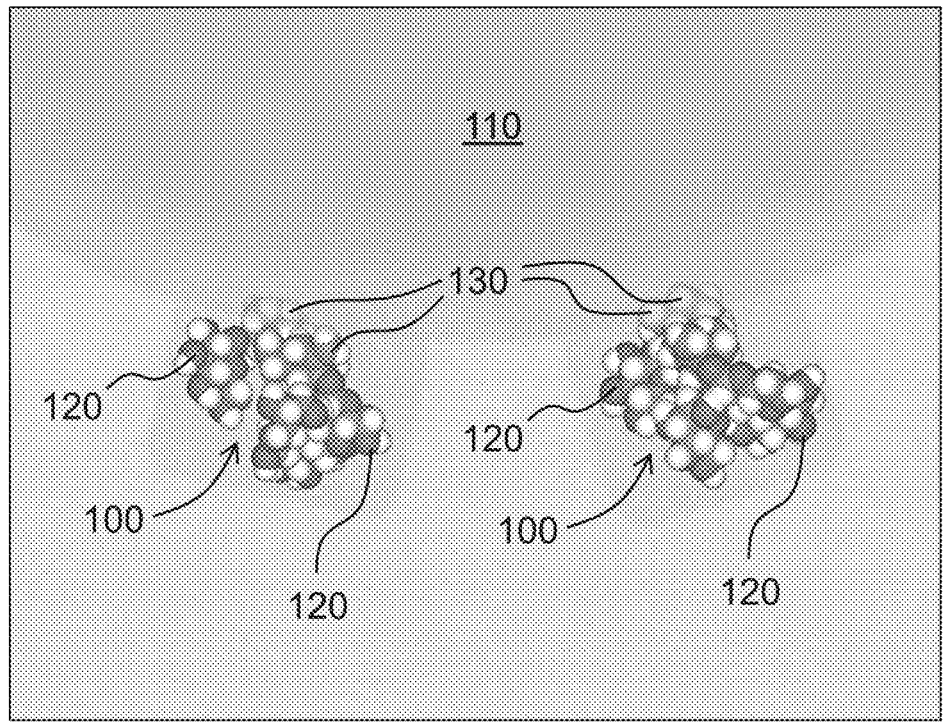
FIG. 1 is a schematic representation of a portion of an organic scaffold particle including a plurality of natural, non-nutritive sweetener molecules aligned thereto in accordance with an aspect of the disclosure.

Aspects of the disclosure relate to a sweetener composition, and food, beverage and pharmaceutical products made therefrom, that include (1) natural, non-nutritive sweetener molecules with an innate flavor profile that includes commercially undesirable tastes, and (2) at least one other naturally derived ingredient(s). The resulting composition has a commercially desirable flavor profile. Exemplary natural, non-nutritive sweeteners may include, but are not limited to, extracts of *stevia* (stevioside, rebaudioside A, rebaudioside B, rebaudioside C, rebaudioside D, rebaudioside E, rebaudioside M, dulcoside), ruboside, monk fruit extracts, mogrosides, mogroside V, neohesperidin dihydrochalcone and combinations thereof.

Natural ingredients that may be combined with the sweetener include oils, lipids, fatty acids, triglycerides, amino acids, peptides, oligopeptides, proteins, protein hydrolysates, carbohydrates, and polysaccharides. In some aspects the natural ingredient is hydrophobic in nature and/or expresses regional or partial hydrophobic properties.

Aspects of the disclosure relate to a sweetener composition including a plurality of assembled particles including natural, non-nutritive sweetener molecules, organic scaffold particles and at least one additive. The natural, non-nutritive sweetener molecules include hydrophilic moieties and hydrophobic moieties. The organic scaffold particles include at least one compositional component including a lipid. The at least one additive includes a surfactant, a stabilizer, an emulsifier, a hydrocolloidal material, a ripening inhibitor, a weighting agent, an excipient, a flavoring agent, a coloring agent, a preservative, a masking agent, a texture enhancer, or a combination thereof.

Further aspects of the disclosure relate to methods for forming a sweetener composition, the sweetener composition including a plurality of assembled particles including natural, non-nutritive sweetener molecules including hydrophilic moieties and hydrophobic moieties, organic scaffold particles including at least one compositional component including a lipid, and at least one additive. The method includes: preparing a solution of the natural, non-nutritive sweetener molecules; and combining the solution with the at least one compositional component and the at least one additive such that the hydrophobic moieties of the natural, non-nutritive sweetener molecules align inward towards a hydrophobic region of the at least one compositional component and the hydrophilic moieties of the natural, non-nutritive sweetener molecules align outward from the at least one compositional component. The at least one additive includes a surfactant, a stabilizer, an emulsifier, a hydrocolloidal material, a ripening inhibitor, a weighting agent, an excipient, a flavoring agent, a coloring agent, a preservative, a masking agent, a texture enhancer, or a combination thereof.

DETAILED DESCRIPTION

The present disclosure can be understood more readily by reference to the following detailed description of the disclosure and the Examples included therein. In various aspects, the present disclosure pertains to sweetener compositions including natural, non-nutritive sweetener molecules and organic scaffold particles including one or more compositional components. Many natural, non-nutritive sweetener molecules have both hydrophilic moieties and hydrophobic moieties within their structure that generally are configured in a manner to minimize free energy and attain the lowest energy state based on their surrounding environment. In the present invention the hydrophobic moieties of the natural, non-nutritive sweetener molecules are aligned inward towards a hydrophobic region of the one or more compositional components of the organic scaffold particles, and the hydrophilic moieties of the natural, non-nutritive sweetener molecules are aligned outward from the organic scaffold particles. In this configuration, the hydrophobic moieties of the sweetener molecules are masked, entrapped or encapsulated by the compositional component(s) of the organic scaffold particles. As used herein, the "scaffold particles" and the one or more compositional components thereof need not be solid or particulate and can include liquid or droplet scaffold particles and compositional components thereof.

In addition, when in an aqueous solution the hydrophobic moieties of the sweetener molecules and compositional component(s) of the organic scaffold particles are shielded from the solution and thus do not interact with the taste receptors of the tongue and oral cavity and its adjacent hydrophobic tissue. Instead, the hydrophilic moieties of the natural, non-nutritive sweetener molecules, which are aligned outward from the organic scaffold particles to preferentially interact with the taste receptors. In addition, this configuration may result in the assembled particle (the organic scaffold particle with its aligned sweetener molecules) having a slightly charged hydrophilic outer shell around the particle. In contrast to the unaligned natural, non-nutritive sweetener molecules, which have a flavor profile that includes commercially undesirable tastes, the sweetener compositions of the present disclosure have a commercially desirable flavor profile.

To improve this temporal taste profile the compositions of the disclosure seek to mask, or in some aspects to entrap or to encapsulate the hydrophobic organic backbone of the natural, non-nutritive sweetener molecule so as to alter, reduce or eliminate its interaction with sweet and bitter taste receptors and adjacent hydrophobic tissue of the tongue and oral cavity, while leaving its sweet portion(s) exposed and available for interaction with the sweet taste receptors. In this way the sweet portion(s) of the natural, non-nutritive sweetener molecule are available to interact with the sweet receptors, while the hydrophobic moieties of the sweetener molecule are unavailable to interact with either the sweet or bitter taste receptors. To mask, entrap or encapsulate the hydrophobic backbone portion and improve the overall taste profile, the disclosure describes a predominately hydrophobic scaffold onto which the sweetener molecules align, with their hydrophobic backbone aligning inwards towards (or entrapped/encapsulated within) the scaffold and their hydrophilic sweet moieties pointing away from the scaffold. Without wishing to be bound by theory, in addition to isolating the hydrophobic backbones of the sweetener molecules, this alignment and molecular orientation minimizes intra- and intermolecular interactions in the sweet-inducing hydrophilic moieties, allowing for more molecular freedom for the moieties to interact with the sweet taste receptors when a solution includes the sweetener composition, or a solid form of the sweetener composition solvates in the mouth and then comes into contact with the tongue and oral cavity of consumers, providing an overall desirable temporal taste profile. In some aspects it is desirable that the hydrophobic scaffold is miscible with the hydrophobic backbone so the sweetener molecules can remain associated with (e.g., masked, entrapped or encapsulated within) the organic scaffold under normal and expected environmental conditions due to hydrophobic effect aggregation.

In other aspects the organic scaffold may include at least two compositional components, where at least one of the compositional components is amphiphilic (i.e., having both a hydrophobic region and hydrophilic region) with its hydrophobic region being miscible with the hydrophobic region of one or more of the other component(s) and where one or more of the hydrophilic regions of these components can form van der Waals attraction and/or hydrogen bonding with portions of an added natural, non-nutritive sweetener molecule in such a manner to assist in properly orienting and anchoring of the sweetener to the compositional component(s) of the scaffold particle. Such organic scaffold particles, which may be referred to as a multi-component organic scaffold particles, may in some aspects be prepared prior to adding the sweetener molecules to the organic scaffold particles. In some aspects the multi-component organic scaffold particles could be formed, at the time of addition of the sweetener molecules.

In further aspects the sweetener molecules could be added to a first portion of organic scaffold particles prior to adding a second portion of organic scaffold particles. Without wishing to be bound by theory, such aspects may facilitate the association (loading) efficiency of the sweetener molecules with the first portion of organic scaffold particles and compositional components thereof, with the second portion of organic scaffold particles and compositional components thereof being added to aid in properly orienting and anchoring of the sweetener molecules to the compositional component(s) of the first portion of organic scaffold particles after the sweetener molecules are hydrophobically encapsulated/aligned to the compositional component(s) of the first portion of organic scaffold particles.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting.

Various combinations of elements of this disclosure are encompassed by this disclosure, e.g., combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

Definitions

It is also to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a natural, non-nutritive sweetener molecule" includes mixtures of two or more natural, non-nutritive sweetener molecules.

As used herein, the term "combination" is inclusive of blends, mixtures, alloys, reaction products, and the like.

Ranges can be expressed herein as from one value (first value) to another value (second value). When such a range is expressed, the range includes in some aspects one or both of the first value and the second value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the designated value, approximately the designated value, or about the same as the designated value. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "one or more optional additional additives" means that the additional additive(s) may or may not be included and that the disclosure includes sweetener compositions that both include and that do not include the additional additive(s).

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Unless otherwise stated to the contrary herein, all test standards are the most recent standard in effect at the time of filing this application.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

Sweetener Compositions

With reference to FIG. 1, aspects of the disclosure relate to a sweetener composition including natural, non-nutritive sweetener molecules 100 and organic scaffold particles 110. The organic scaffold particles 110 include one or more compositional components (e.g., caprylic acid and palmitic acid as fatty acid compositional components of coconut oil). The natural, non-nutritive sweetener molecules 100 include hydrophilic moieties 120 and hydrophobic moieties 130. The hydrophobic moieties 130 of the natural, non-nutritive sweetener molecules 100 are aligned inward towards a hydrophobic region of the one or more compositional components of the organic scaffold particles 110, and the hydrophilic moieties 120 of the natural, non-nutritive sweetener molecules 100 are aligned outward from the organic scaffold particles 110. In this manner, the temporal taste profile of the sweetener compositions is improved because the hydrophobic backbone of the natural, non-nutritive sweetener molecule 100 is masked, entrapped or encapsulated so as to alter, reduce or eliminate its interaction with sweet and bitter taste receptors of the tongue and oral cavity, while leaving its sweet hydrophilic portion(s) exposed and available for interaction with the sweet taste receptors. To mask, entrap or encapsulate the hydrophobic backbone portion and improve the overall taste profile, the disclosure describes organic scaffold particles 110 onto which the sweetener molecules align, with their hydrophobic backbone aligning inwards towards one or more compositional components of the organic scaffold particle 110 (or encapsulated within it as illustrated in FIG. 1) and their hydrophilic sweet moieties pointing away from the organic scaffold particle 110. It is believed that in addition to isolating the hydrophobic backbones of the sweetener molecules, this alignment and molecular orientation minimizes intra- and intermolecular interactions in the sweet inducing hydrophilic moieties, allowing for more molecular freedom for the moieties to interact with the sweet taste receptors when a solution includes the sweetener composition, or a solid form of the sweetener composition solvates in the mouth and then comes into contact with the tongue and oral cavity of consumers, providing an overall desirable temporal taste profile. Without wishing to be bound by theory, the sweetener composition in some aspects minimizes activation of bitter receptors in the oral cavity by masking, entrapping or encapsulating the sweetener's hydrophobic isoprenoid backbone within the matrix of the organic scaffold particle, while simultaneously allowing for a less encumbered activation of the sweet receptors in the oral cavity because the organic scaffold particles are surrounded by numerous sweet-inducing (glucose in the case of *stevia* and monk fruit) hydrophilic moieties, forming a sweet protective and slightly charged hydrophilic outer shell to the particles. In addition, it is believed that simply reducing activation of bitter receptors increases the sensation of sweetness, as noted in Hellfritsch et al., Human psychometric and taste receptor responses to steviol glycosides, J. Agric. Food Chem., Jul. 11, 2012, the disclosure of which is incorporated herein by this reference in its entirety. The improved sensation of sweetness and temporal taste profile of the disclosed sweetener composition may reduce the amount of sweetener required to be added to establish desirable organoleptic profiles of the sweetened food, beverage nutritional and pharmaceutical products, resulting in taste, economic and nutritional benefits.

In some aspects the natural, non-nutritive sweetener molecules 100 include extracts of *stevia*, monk fruit extracts, mogrosides, neohesperidin dihydrochalcone and combinations thereof. Exemplary extracts of *stevia* include stevioside, rebaudioside A, rebaudioside B, rebaudioside C, rebaudioside D, rebaudioside E and rebaudioside M, dulcoside, rubusoside and combinations thereof. In particular aspects the natural, non-nutritive sweetener molecules 100 include steviol glycosides, such as rebaudioside A or mogrosides, such as mogroside V, which can be found in, e.g., *Stevia rebaudiana* (Bertoni) leaves, monk fruit (luo han guo) and the Chinese plant *Rubus chingii*.

The organic scaffold particles 110 can include any material that, when combined with the natural, non-nutritive sweetener molecules 100, will mask, entrap, encapsulate or otherwise influence the hydrophobic backbone of the natural, non-nutritive sweetener molecule 100 and leave the sweet hydrophilic portion exposed so as to improve the taste profile—or more generally any organoleptic property—of the sweetener composition. In certain aspects the organic scaffold particles 110 are predominately hydrophobic, and each may include a hydrophobic core.

In some aspects the organic scaffold particles 110 include compositional components that may include: coconut oil extracts; sunflower oil; canola oil; soybean oil; vegetable oil; avocado oil; safflower oil; grapeseed oil; hazelnut oil; almond oil; cashew oil; nut oil; castor oil; medium chain (e.g., 6-12 or 6-10 carbon atoms) glycerides including (monoglycerides, diglycerides, triglycerides), unsaturated or saturated plant or animal-based fats, fatty acids, oils or butters; amino acids, peptides; oligopeptides, proteins, protein hydrolysates, carbohydrates; polysaccharides; natural or synthetic polymers; and any combination thereof. Such compounds may be particularly useful as organic scaffold particles because they do not appreciably contribute to and/or detract from the flavor profile of sweetener compositions including the particles.

In other aspects the organic scaffold particles include compositional components that may include: edible essential oils; flavor-based oils, including orange oil, lemon oil, lime oil, cinnamon oil and vanilla oil; flaxseed oil; olive oil; rapeseed oil; omega 3 oil; omega 6 oil; omega 9 oil; fish oils; krill oils; long chain oils, fats, fatty acids, monoglycerides, diglycerides, or triglycerides; and any combination thereof.

These compounds may be less desirable for use in sweetener compositions according to the disclosure, however, as they can provide stronger flavor contributions to compositions including them.

In yet further aspects the organic scaffold particles include compositional components that may include any combination of the previously mentioned materials.

Figure 3:
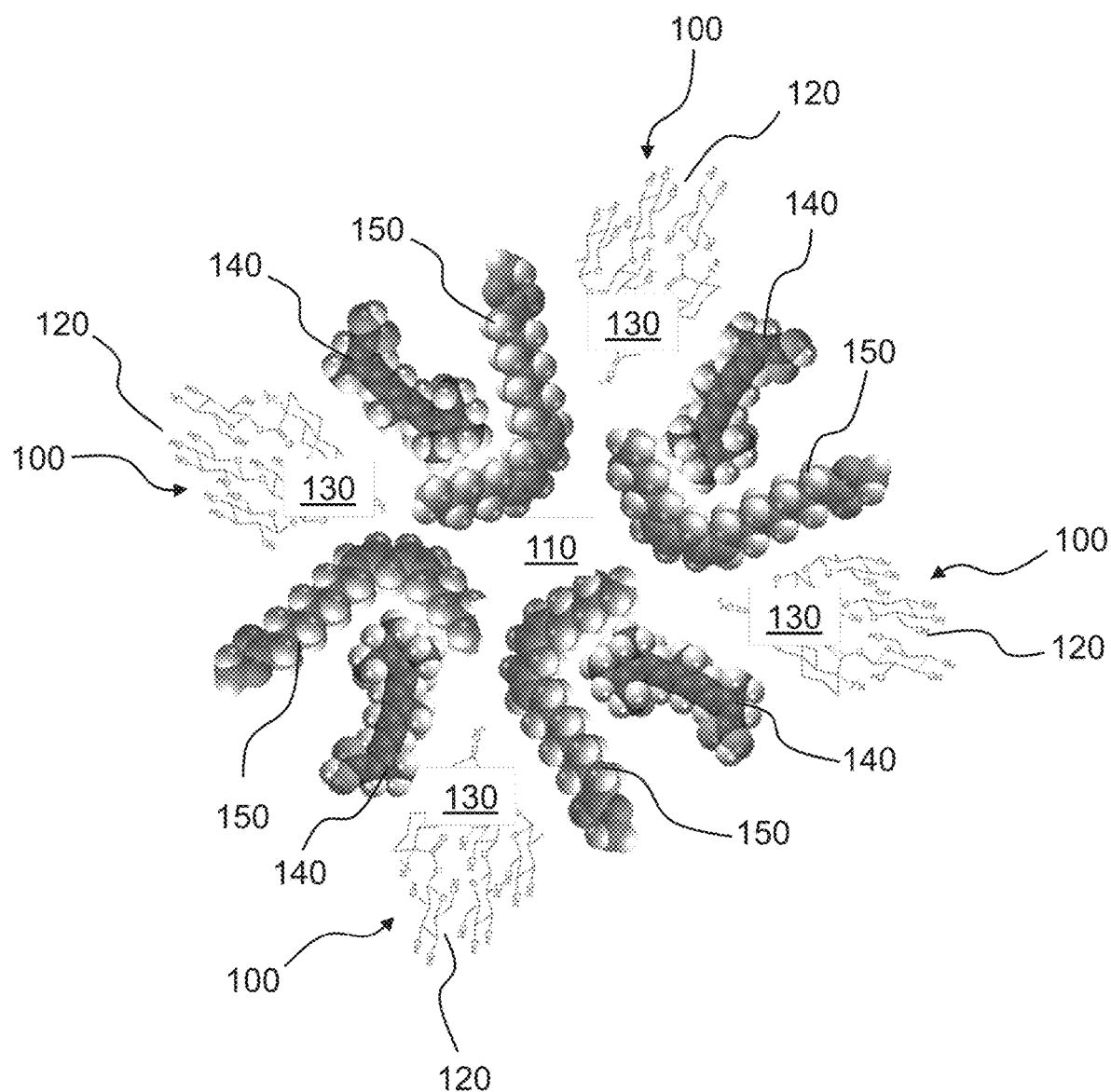
FIG. 3 is a schematic representation of exemplary compositional components of an organic scaffold particle having a plurality of sweetener molecules aligned thereto in accordance with an aspect of the disclosure.
Figure 4:
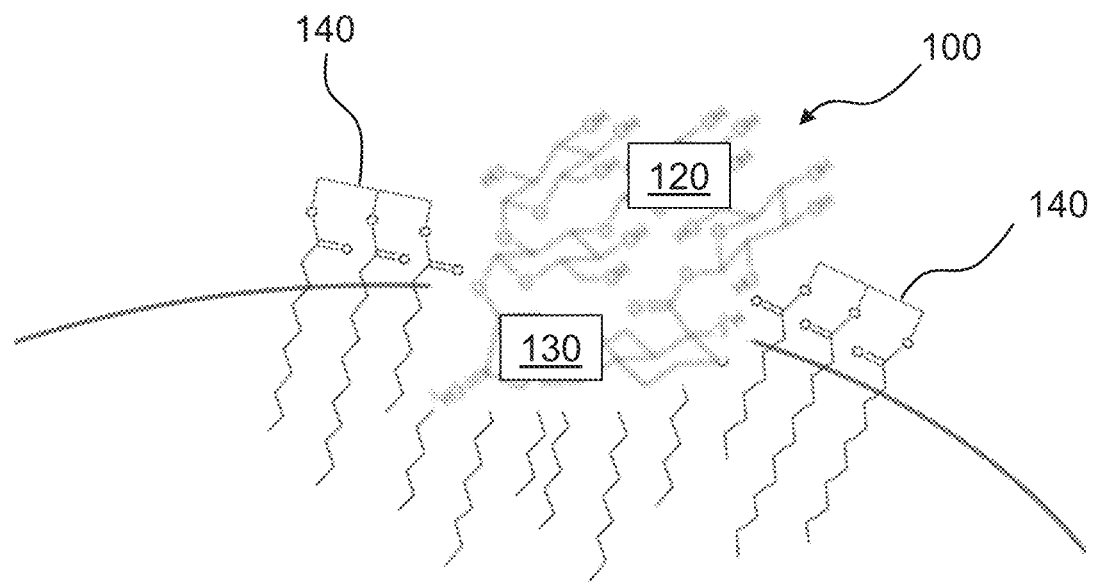
FIG. 4 is a schematic representation of exemplary compositional components of an organic scaffold particle having a sweetener molecule aligned thereto in accordance with an aspect of the disclosure.

In particular aspects the organic scaffold particles 110 include one or more medium chain glycerides as compositional components. In some aspects the medium chain glyceride is a triglyceride. In specific aspects the medium chain glyceride is a C6-C10 medium chain glyceride. The medium chain glyceride may further include medium chain monoglycerides and/or medium chain diglycerides in some aspects. In a specific aspect the organic scaffold particles 110 include a medium chain triglyceride derived from coconut oil. Medium chain triglycerides (MCTs) (e.g., caprylic acid C8:0) derived from coconut oil have been found to be of sufficient size and composition to mask, entrap or encapsulate the natural non-nutritive sweetener molecules 100 and remain stable in solution, while providing a minimal contribution to the flavor profile of the sweetener compositions. FIGS. 3 and 4 illustrate exemplary compositional components of an organic scaffold particle 110 having a plurality of sweetener molecules 100 aligned thereto in accordance with an aspect of the disclosure. The exemplary organic scaffold particle 110 includes a plurality of compositional components 140, 150, which in the illustrated example include two different medium chain fatty acids. The sweetener molecules 100 include hydrophobic moieties 130 aligned inward towards a hydrophobic region of the compositional components 140, 150 of the organic scaffold particle 110, and hydrophilic moieties 120 aligned outward from the compositional components 140, 150 of the organic scaffold particle 110.

In certain aspects the medium chain glyceride—and in particular the C6-C10 medium chain glyceride includes at least 20 wt % of the total lipid content of the sweetener composition. In particular aspects the medium chain glyceride includes from 20 wt % to 100 wt % of the total lipid content, or from 30 wt % to 100 wt % of the total lipid content, or from 40 wt % to 100 wt % of the total lipid content, or from 50 wt % to 100 wt % of the total lipid content, or from 60 wt % to 100 wt % of the total lipid content, or from 70 wt % to 100 wt % of the total lipid content, or from 80 wt % to 100 wt % of the total lipid content, or from 90 wt % to 100 wt % of the total lipid content.

Depending on the composition of the food, beverage, nutritional, or pharmaceutical product the sweetener is added to, there may be incidences where the desired compositional components of the organic scaffold particles are already a component of the unsweetened food, beverage, nutritional, or pharmaceutical product and therefore allowing for those components to be used in the construction of the scaffold particles to reduce alterations to the overall organoleptic properties of the food, beverage, nutritional, or pharmaceutical product containing the sweetener composition.

In some aspects the organic scaffold particles are generally spherical in shape. It is believed that a spherically-shaped scaffold particle allows hydrophobically masked/entrapped/encapsulated natural, non-nutritive sweetener molecules 100 to better uniformly organize on the organic scaffold particle 110 and to support non-congested radial extensions of the sweet inducing hydrophilic moieties of the sweetener molecules 100. In addition, the combined total surface area of many small spheres is large, allowing maximal exposure of the hydrophilic sweet moieties for improved sweetness profile relative to the amount of sweet molecules present.

In certain aspects the organic scaffold particles have a particle size of from about 1 nanometer (nm) to about 10 microns ($\mu m$), and in more particular aspects of from about 10 nm to about 1 $\mu m$, or from about 20 nm to about 1 $\mu m$, or from about 30 nm to about 1 $\mu m$, or from about 40 nm to about 1 $\mu m$, or from about 50 nm to about 1 $\mu m$, or from about 100 nm to about 1 $\mu m$, or from about 50 nm to about 500 nm.

As discussed, the hydrophobic moieties 130 of the natural, non-nutritive sweetener molecules 100 are aligned inward towards a hydrophobic region of the one or more compositional components of the organic scaffold particles 110, and the hydrophilic moieties 120 of the natural, non-nutritive sweetener molecules 100 are aligned outward from the organic scaffold particles 110 (and the one or more compositional components thereof). The one or more compositional components of the organic scaffold particles 110 may be predominately hydrophobic, and in some aspects the hydrophobic moieties 130 of the natural, non-nutritive sweetener molecules 100 are aligned inward towards a hydrophobic region of the one or more compositional components of the organic scaffold particles 110 by hydrophobic/hydrophilic forces. The hydrophobic/hydrophilic forces may in some aspects be hydrophobic effect aggregation forces. In other aspects the hydrophobic/hydrophilic forces are van der Waals forces. In certain aspects the hydrophobic moieties 130 of the natural, non-nutritive sweetener molecules 100 are aligned inward towards a hydrophobic region of the one or more compositional components of the organic scaffold particles 110 by hydrogen bonding.

The organic scaffold and assembled particles have one or more desirable properties. In particular, in certain aspects the organic scaffold particles: provide adequate dispersional properties in a water solution alone, upon agitation, with the addition of dispersion agents, or a combination thereof to promote efficient loading of the natural, non-nutritive sweetener molecules to the organic scaffold through hydrophobic aggregation, self-assembly, van der Waals forces and/or hydrogen bonding. The organic scaffold particles anchor and orient the natural, non-nutritive sweetener molecules in the desired orientation. Whereas, the assembled particles, containing the organic scaffold and natural, non-nutritive sweetener molecules are able to maintain longer term colloidal stability of the small, micro, or nano-sized particles in solution and maintain particle integrity when traversing the tongue and oral cavity. Further, the assembled particles in solution or in a dry powdered state maintain chemical composition and integrity over an extended shelf life period; contribute minimal, or desired flavor contributions and/or support and not negatively interfere with the desired organoleptic properties of the final composition; and any combination thereof.

In other aspects the hydrophobic moieties 130 of the natural, non-nutritive sweetener molecules 100 are covalently bonded to one or more compositional components of the organic scaffold particles 110. This may be particularly desirable if the compositional component is an amino acid, peptide, oligopeptides, proteins, protein hydrolysates, carbohydrate, polysaccharide or either a natural or synthetic polymer. If the compositional component is a solid or gel at storage, shipping and mouth temperatures, or is a highly branched or physically dense carbohydrate, polysaccharide oligopeptide, protein, protein hydrolysate, or synthetic polymer, then in addition to, or in place of chemical attractive forces, the natural, non-nutritive sweetener may be physically entrapped or encapsulated within the organic scaffold particle 110.

Without wishing to be bound by theory, it is believed that absent an organic scaffold to hydrophobically aggregate with, solubilized amphiphilic sweetener molecules, seeking their lowest energy state, will cluster together in small numbers in the aqueous environment such that their hydrophobic portions point towards each other and their hydrophilic portions face outward, until reaching a steric hinderance limit to the size of the aggregates. It is believed these small sterically congested sweetener clusters contribute to the delayed onset and lingering perceived sweetness found with simple aqueous natural, non-nutritive sweetener solutions. It is further believed these clusters, or individual sweetener molecules allow their hydrophobic regions to interact with the bitter receptors and contribute to the perceived lingering bitter aftertaste. Providing organic scaffold particles of appropriate size and composition to an aqueous solution of solubilized sweetener molecules the scaffold particles offers a preferred nucleation and support structure for sweetener molecules to hydrophobically aggregate with and attach to. Depending on the shape and size of the organic scaffold particle and the ratio of sweetener molecules to available total scaffold particle surface area, it is believed a substantially higher number of sweetener molecules can aggregate together (per particle) than the naturally-occurring clusters, though in a more organized and less molecularly congested format. It is further hypothesized that the spherical shape of the organic scaffold particle (if so configured) allows the hydrophilic portion of the natural, non-nutritive sweetener molecules to better distribute uniformly and radiate outwardly. Particular aspects of the disclosure include spherical organic scaffold particles less than 1 μm in size and in which the number of natural, non-nutritive sweetener molecules is equal to or less than the number required to saturate the total surface area of the organic scaffold particles in the solution. This configuration allows the organic scaffold particles to provide greater sweetener molecular spacing (reduced molecular congestion), improve alignment of the sweet moieties, and better encapsulate the hydrophobic portions of the sweetener molecule. This greater spacing between individual sweetener molecules than that which is found with aqueously solvated naturally clustering sweetener molecules allows for less inter- and intramolecular interactions between the branches of the sweet moieties and more freedom to interact unencumbered with the sweet receptors. This unencumberment, along with the hydrophilic shell of the assembled particles shielding access to hydrophobic moieties, may provide an explanation as to why sweetener compositions according to the disclosure have an observed earlier perceived sweetness onset, shorter lingering sweetness profile and reduced or no bitter, astringent, licorice, metallic or chemical taste, or aftertaste than that observed with a simple aqueous solution of natural, non-nutritive sweetener molecules.

Some natural, non-nutritive sweetener extracts may have an undesirably small level of hydrophobic bitter impurities. Therefore, in certain aspects the number of natural, non-nutritive sweetener molecules is less than the number required to saturate the total surface area of the organic scaffold particles in the solution to allow the hydrophobic impurities to be masked or encapsulated within the scaffold particle structure and be isolated from interacting with either the sweet or bitter receptors.

Figure 5:
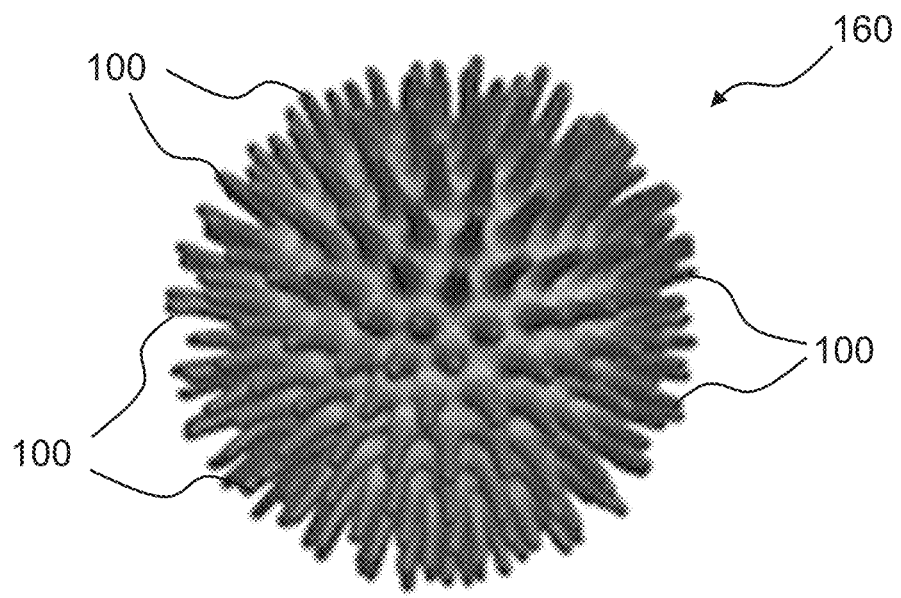
FIG. 5 is a representation of an exemplary assembled particle including an organic scaffold particle having its surface area substantially populated by natural, non-nutritive sweetener molecules in accordance with an aspect of the disclosure.

The organic scaffold particle 110 including one or more compositional components having natural, non-nutritive sweetener molecules 100 aligned thereto is collectively referred to herein as an assembled particle 160. An exemplary assembled particle 160 is illustrated in FIG. 5.

In some aspects a sufficient number of the hydrophobic moieties 130 of the natural, non-nutritive sweetener molecules 100 are aligned inward towards a hydrophobic region of the one or more compositional components of the organic scaffold particles 110 so as to substantially populate the surface area of the assembled particle. As used herein, "substantially populate" means that at least about 50%, or at least about 60%, or at least about 70%, or at least about 80%, or at least about 85%, or at least about 90%, or at least about 92%, or at least about 95%, or at least about 98%, or at least about 99% of the surface area of the assembled particle is populated with—or covered by—the natural, non-nutritive sweetener molecules. In particular aspects "substantially populate" means that at least about 90% of the surface area of the assembled particle is populated with—or covered by—the natural, non-nutritive sweetener molecules. The assembled particle 160 illustrated in FIG. 5 has its surface area substantially populated by natural, non-nutritive sweetener molecules 100.

Figure 6:
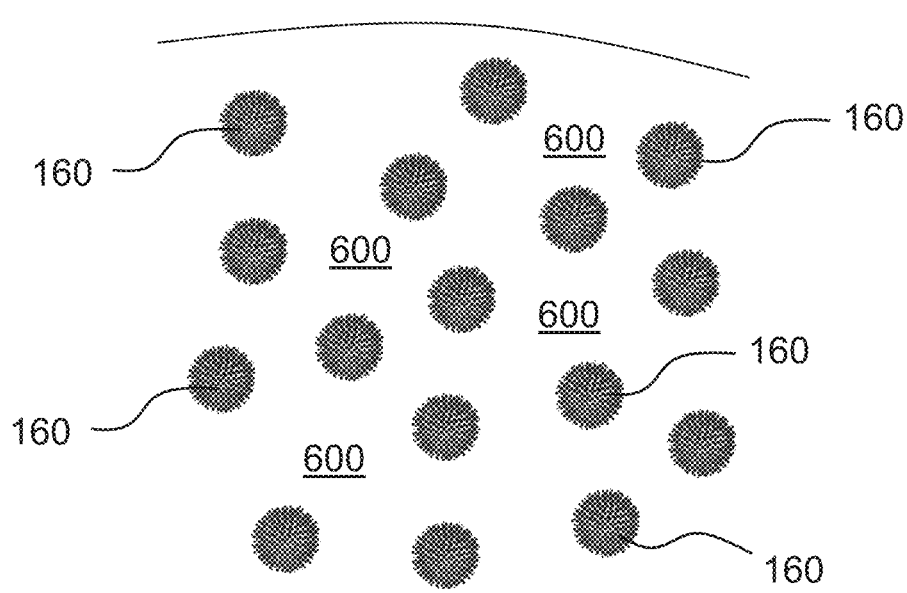
FIG. 6 is a schematic representation of an emulsion including a plurality of assembled particles, each of which includes an organic scaffold particle having its surface area substantially populated by natural, non-nutritive sweetener molecules in accordance with an aspect of the disclosure.

In some aspects of the sweetener composition in which the composition is in the form of an emulsion or suspension the natural, non-nutritive sweetener acts as the emulsifier to the hydrophobic organic scaffold particles to stabilize the resulting assembled particles in the aqueous solution/emulsion. FIG. 6 illustrates an exemplary emulsion 600 including a plurality of assembled particles 160 contained therein. As described above the assembled particles 160 may have slightly charged hydrophilic outer shell. As a result, individual assembled particles 160 repel each other and don't combine and cause separation or collapse of the emulsion.

In further aspects the sweetener composition includes one or more additional additives, which may in certain aspects be hydrophilic, hydrophobic or amphiphilic. The one or more additional additives may include a surfactant, a stabilizer, an emulsifier, a hydrocolloidal material (such as but not limited to gum), a ripening inhibitor, a weighting agent, an excipient, a flavoring agent, a coloring agent, a preservative, a masking agent, a texture enhancer, or a combination thereof. It may be desirable in some aspects that the one or more additional additives be derived from a natural source so that the overall sweetener composition remains natural.

The one or more additional additives may be included in the sweetener composition to improve the final form taste, appearance, performance and/or stability of the composition. In further aspects the one or more additional additive includes a substance to either support or prevent the additives from interfering with or coalescing with the natural, non-nutritive sweetener molecules, the organic scaffolding particles and/or the assembled particles. The one or more additional additives may further provide and/or enhance the desired flavor and/or mouth-feel features, mask or block unwanted flavors or temporal taste profiles, provide overall solution stability, and/or improve the final appearance of the solution. In particular aspects the one or more additional additives include an excipient, such as a polysaccharide, a carbohydrate or a dietary fiber is added to give the final solution "mouth-feel" texture similar to a sucrose sweetened solution. Desirable "mouth-feel" excipients may include: natural fibers, inulin, dextrin or maltodextrin.

The sweetener composition may be added to a range of food, beverage nutritional and pharmaceutical products that require certain compositions and/or environmental conditions, such as other ingredients or environmental conditions (temperature, pH, etc.) that may interfere with the stability and/or performance of the sweetener composition. Therefore, in some aspects specific combinations of the above organic scaffold compositional components and natural non-nutritive sweeteners additional additives may be used to maintain the stability and performance of the sweetener composition.

The sweetener composition may be in any physical form that allows the hydrophobic moieties 130 of the natural, non-nutritive sweetener molecules 100 to align inward towards a hydrophobic region of the one or more compositional components of the organic scaffold particles 110 and align the hydrophilic moieties 120 of the natural, non-nutritive sweetener molecules 100 outward from the one or more compositional components of the organic scaffold particles 110. In a particular aspect the composition is in the form of an emulsion or suspension. In other aspects the composition is in the form of a liquid. The emulsion, suspension or liquid may include solubility, miscibility, stability enhancers and/or weighting agents to facilitate keeping the components of the composition in solution. In other aspects the emulsion, suspension or liquid acts as the solubility enhancer for the sweetener molecules. In certain aspects the sweetener composition may be in the form where the assembled particles are partially in contact with a gas. In this form the hydrophobic moieties 130 of the natural, non-nutritive sweetener molecules 100 align towards a hydrophobic region of the one or more compositional components of the organic scaffold particles 110 and the hydrophilic moieties 120 of the natural, non-nutritive sweetener molecules 100 are aligned into the gas. This form of the sweetener composition may be applicable in gas-loaded beverages and at liquid/gas interfaces.

In other aspects the sweetener composition is in the form of a solid, and in particular aspects the solid is a dry powder. The solid sweetener can be used by reconstituting it into a solution form prior to consumption, singly or as part of a food, beverage, nutritional or pharmaceutical product, or consumed as a solid singly or as part of a food, nutritional or pharmaceutical product wherein the solid sweetener reconstitutes to a solution within the oral cavity. The solid form of the sweetener can further be incorporated as a component of a solid food, nutritional or pharmaceutical product, such as products formed by compressing, binding or shearing powders together, or where the dried assembled particles contain at least one component of the food, beverage, nutritional or pharmaceutical product. The form of the sweetener composition can be comprised to be stable at any number of temperature conditions, including but not limited to room temperature, mouth temperature, and storage temperature and serving temperature. In addition, the sweetener composition may take the form of a homogeneous or inhomogeneous solid, a layered composition and an interconnecting matrix, and may be in the form of any desirable shape. The matrix may be a solid matrix or in a liquid form, and includes lipids that are solid at room and body temperatures.

In certain aspects the sweetener composition is a lipid-in-water composition including: natural, non-nutritive sweetener molecules; a continuous aqueous phase; and a discontinuous lipid phase including a C6-C10 medium chain glyceride. In further aspects the C6-C10 medium chain glyceride includes at least 20 wt % of the total lipid content of the sweetener composition. As used herein, a "continuous aqueous phase" has its customary meaning according to those skilled in the art and includes the aqueous (e.g., water-based) portion of the composition that suspends the lipid phase in the composition. As used herein, a "discontinuous lipid phase" has its customary meaning according to those skilled in the art and includes the lipid/oil in the composition that is immiscible in—and suspended within— the continuous aqueous phase.

In a specific aspect the sweetener composition includes: natural, non-nutritive sweetener including rebaudioside A; the organic scaffold particles include at least one compositional component including a C8 medium chain triglyceride derived from coconut oil having a generally spherical shape and a particle size of from about 10 nm to about 1 µm; and the sweetener composition is in the form of an emulsion.

In some aspects the sweetener composition provides an improved or more commercially acceptable organoleptic taste profile as compared to a substantially identical sweetener composition comprising the same natural, non-nutritive sweetener molecules but that does not include the organic scaffold particles.

In further aspects the sweetener composition utilizes the natural, non-nutritive sweetener molecules more efficiently, resulting in a lower amount of sweetener required to reach a desired sweetness level, providing added economic, ecological footprint and health benefits over natural, non-nutritive sweetener formulations that do not include the organic scaffold particles.

The sweetener composition according to the disclosure may be incorporated into a food, beverage, nutritional or pharmaceutical product. In certain aspects the food product includes a baked good, a sauce, a dairy product (such as but not limited to ice cream, yogurt and cheese), a protein shake, a protein bar, a cereal, a canned food, a frozen food, a chocolate product (e.g., a naturally sweetened artisan chocolate bar), a functional food, a processed food, confections, or a candy. Exemplary nutritional products include, but are not limited to, a vitamin or a nutritional supplement. Exemplary pharmaceutical products include, but are not limited to, an orally administered pharmaceutical or a concentrated or dried product that may be reconstituted into one of the foregoing products. Exemplary beverages that the sweetener compositions of the disclosure may be incorporated into include, but are not limited to, soda, tea, juice, coffee, a dairy beverage (e.g., milk), a health drink, a chocolate drink, an energy drink and flavored water. For ready to mix and ready to drink products, the sweetener composition can be prepared to the desired level of sweetness and added to the typical array of flavors, additives and preservatives common among these prepackaged products. Exemplary pharmaceutical products in which the sweetener composition could be incorporated include, but are not limited to, orally administered chewable, lozenge, thin film or drinkable pharmaceutical compositions that include sweeteners such as cough drops, cold and cough syrups, liquid antibiotics, and the like. In certain aspects the sweetener can be added with other sweeteners to a food, beverage, nutritional or pharmaceutical product to provide a collective sweetness taste profile to the item. The food, beverage, nutritional or pharmaceutical product may be a concentrated or dried product that may be reconstituted into one of the foregoing products.

The sweetener compositions of the disclosure can also be sold as a stand-alone product to be added to a "homemade" beverage or food product as a replacement for sucrose, artificial sweeteners, or other naturally-derived sweeteners. Such example beverages or food products include but are not limited to brewed tea or coffee, fresh-squeezed lemonade, cakes, pies, puddings, and pastries. In these cases the sweetener composition (in the form of, e.g., an emulsion, suspension, liquid, or dry powder) may be packaged within any number of suitable, industry standard containment systems for shelf storage. It may be desirable in such aspects that the sweetener composition be compatible with and added to a wide variety of beverage, food, nutritional or pharmaceutical products.

The compatibility of the sweetener composition with the beverage/food/nutritional/pharmaceutical product may be affected by the pH of the product. For example, some organic scaffold particles or compositional components thereof may be soluble in certain beverage products but not others. Solubility of the sweetener composition may be dependent at least in part on the pH of the product. Accordingly, it may be desirable in some aspects to select organic scaffold particles or compositional components thereof so that the sweetener composition will be compatible with the pH of the end product. While the sweetener composition may have any desirable pH, in particular aspects the sweetener composition has a pH of from about 2.5 to about 9. In certain aspects the sweetener composition is stable across this pH range; in other words the stability of the composition, the taste profile of the composition, or other organoleptic properties of the composition are not affected by pH changes within this range.

In some aspects the taste profile (or more generally any organoleptic property profile) of sweetener compositions according to aspects of the disclosure is not dependent on the beverage or food system in which the sweetener composition is used, unlike the taste profile delivered by conventional natural non-nutritive sweetener products. Without being bound by theory, it is believed that sweetener compositions according to the present disclosure can deliver a consistent sugar-like taste profile in a wide range of environmental conditions (temperature, pH, etc.) because the configuration of the assembled particles, having a substantially populated outer shell of sugar molecules surrounding—and at least significantly, isolating—non-sugar moieties of the particles from the solutions, will exhibit overall properties similar to its exposed sugars under these various environmental conditions.

Methods for Making Sweetener Compositions

Aspects of the disclosure further relate to methods for forming a sweetener composition including assembled particles, the assembled particles including natural, non-nutritive sweetener molecules and organic scaffold particles including one or more compositional components. The natural, non-nutritive sweetener molecules include hydrophilic moieties and hydrophobic moieties. The method includes: preparing a solution of the natural, non-nutritive sweetener molecules; and combining the solution with the organic scaffold particles such that the hydrophobic moieties of the natural, non-nutritive sweetener molecules align inward towards a hydrophobic region of the one or more compositional components of the organic scaffold particles and the hydrophilic moieties of the natural, non-nutritive sweetener molecules align outward from the one or more compositional components of the organic scaffold particles.

Figure 2:
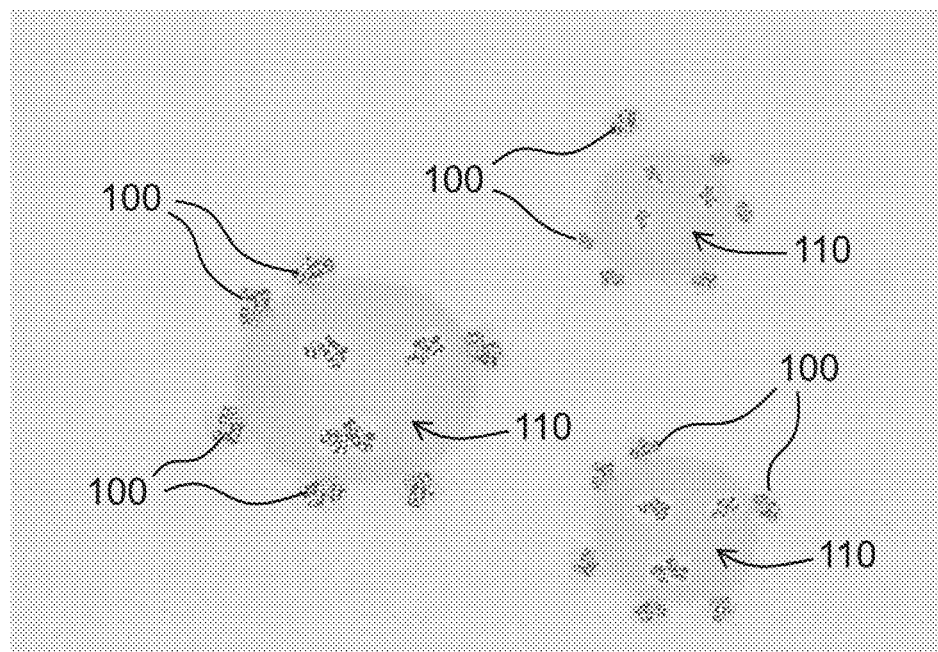
FIG. 2 is a schematic representation of organic scaffold particles and a plurality of natural, non-nutritive sweetener molecules aligned thereto in accordance with an aspect of the disclosure.

In some aspects the organic scaffold particles are preformed in an "organic particle in liquid" suspension. The organic scaffold particles may be broadly characterized as including a carbon-based chemical substance, and more specifically of a natural product origin. The one or more compositional components of the organic scaffold particles 110 may have hydrophobic or partially hydrophobic properties and be at least somewhat miscible with organic portions of the natural, non-nutritive sweetener molecules 100, as illustrated in FIG. 2. In other aspects, the organic scaffold particles could include other organic substances capable of encapsulating portions of the natural, non-nutritive sweetener molecules, including but not limited to oils, lipids, fatty acids, triglycerides, amino acids, peptides, oligopeptides, proteins, protein hydrolysates, carbohydrates, and polysaccharides. In yet other aspects, the organic scaffold particles include at least one compositional component that will form independently and/or in cooperation with the natural, non-nutritive sweetener, self-assembled particles of desired size and dispersion when added to a water solution. In particular aspects, the formation, size and dispersion of the organic scaffold particles will be created by high shear homogenization of a hydrophobic or partially hydrophobic substance in a water solution. An example of this is an emulsion where oil droplets are stabilized and dispersed in an aqueous environment.

Selection of the homogenization method and amount of shear affects the size range and dispersion of the organic scaffold particles in solution. In some aspects the organic scaffold particles and compositional components thereof are processed to achieve a size range that maximizes loading of the natural, non-nutritive sweetener molecules onto the particles and to maintain solution stability and a desired final temporal taste or organoleptic property profile. In certain aspects the organic scaffold particles provide one or more of the following functions:

(1) provide adequate total particle surface area to support transfer of a high concentration of natural, non-nutritive sweetener molecules to the organic scaffold particles in the desired orientation;

(2) sufficiently mask, entrap or encapsulate the hydrophobic backbones of the natural, non-nutritive sweetener molecules;

(3) when a component of assembled particles will support sweet inducing moiety separation (i.e., hydrophilic moieties) of the natural, non-nutritive sweetener molecules;

(4) when a component of assembled particles will allow for access and proper ligand orientation and presentation to sweet taste receptors on the tongue and in the oral cavity;

(5) when a component of assembled particles will provide a configuration not conducive for bitter receptor activation on the tongue and oral cavity;

(6) when a component of assembled particles will provide a configuration not conducive for delayed activation to sweet receptors on the tongue and oral cavity;

(7) reduce astringency, licorice, metallic and chemical taste and lingering aftertaste;

(8) when a component of assembled particles will provide a configuration not conducive for lingering activation to sweet receptors on the tongue and oral cavity; and (9) when a component of assembled particles will provide long-term stability of the sweetener composition (e.g., emulsion, suspension, liquid or dry powder).

In certain aspects the organic scaffold particles have a particle size of from about 1 nanometer (nm) to about 10 microns (µm), and in more particular aspects of from about 10 nm to about 1 µm, or from about 20 nm to about 1 µm, or from about 30 nm to about 1 µm, or from about 40 nm to about 1 µm, or from about 50 nm to about 1 µm, or from about 100 nm to about 1 µm, or from about 50 nm to about 500 nm. While not intending to be limiting, it is believed that very small particles, with their greater surface curvature, aided by the hydrophobic/hydrophilic interface being at or near the base of the sweet inducing moieties of the natural, non-nutritive sweetener molecules, provide for maximal radial physical separation between the sweet inducing moieties and lower steric hindrance and intermolecular hydrogen bonding between moieties. Thus when the organic scaffold particles form assembled particles they will collectively allow for improved sweet receptor accessibility and an increased rate of binding and unbinding from the sweet receptors to yield a temporal taste profile closer to that of a sugar (sucrose)-sweetened solution. In addition, as is well known in the art, smaller particles allow for the appearance of a clear solution (e.g., emulsion, suspension or liquid), if such a solution is desired.

In addition to the assembled particles, one or more optional additional additives can be added to the sweetener composition to enhance the overall properties of the composition. The one or more additional additives may be hydrophilic, amphiphilic or hydrophobic, and in some aspects may be derived from natural sources. These can be added either before loading of the natural, non-nutritive sweetener molecules onto the organic scaffold particles or after, which may be advantageous if the natural, non-nutritive sweetener molecules load more efficiently onto organic scaffold particles with a first portion of organic scaffold particles and compositional components thereof, with the second portion of organic scaffold particles and compositional components thereof being added to aid in properly orienting and anchoring of the sweetener molecules to the compositional component(s) of the first portion of organic scaffold particles after the sweetener molecules are hydrophobically encapsulated/aligned to the compositional component(s) of the first portion of organic scaffold particles. For example, after the natural, non-nutritive sweetener molecules are loaded onto the organic scaffold particles, a second, polar, or more polar amphiphilic organic substance may be added that gives the assembled particles a surface change that could help anchor the natural, non-nutritive sweetener molecules to the organic scaffold particles. An added surface charge may also be advantageous in helping to set the appropriate overall net charge of the assembled particles to facilitate particle-to-particle repulsion to enhance particle dispersion and overall solution stability by minimizing coalescence of the assembled particles. In addition to the innate properties of the assembled particles in solution, additional additives may also be added to the solution to enhance its overall solution properties. Exemplary optional additional additives include, but are not limited to, surfactants or other suspension stabilizing agents, such as weighting agents, a hydrocolloidal material (such as but not limited to gum), ripening inhibitors, carbonation, emulsifiers, flavoring agents, preservative, masking agents, texture enhancers, excipients (including but not limited to dextrin, lecithin, casein, inulin, xanthan gum, gum Arabic and/or oligopeptides) and a combination thereof. Such optional additional additives may also be added to the final solution to support suspension stability. In particular aspects the natural non-nutritive sweetener is the emulsifying agent. In further particular aspects the one or more optional additional additives are selected such that they do not add to a taste profile inconsistent with the overall desired taste preference of the finished sweetener composition.

Many known natural, non-nutritive sweeteners have poor solubility in aqueous solutions, including the *stevia* glycosides such as Rebaudioside A. Thus, in order to maximize the number and/or amount of solubilized natural, non-nutritive sweetener molecules available to load from an aqueous solution onto organic scaffold particles and establish a high concentration sweetener solution it may be desirable to include one more additional solvents and/or processing methods to the solution. One or more additional solvents can be added, or one or more additional processing methods can be performed, just prior to or at the time of combining the natural, non-nutritive sweetener molecules with the organic scaffold particles in order to increase the solubility of the natural, non-nutritive sweetener molecules and thus the number of molecules available for loading. In some aspects the additional solvent(s) and/or additional method(s) may be temporarily applied to the solution to increase solubility, dispersion, miscibility and self-assembly (loading) of the natural, non-nutritive sweetener molecules onto the organic scaffold particles. As referenced above, after the natural, non-nutritive sweetener molecules are successfully loaded onto the organic scaffold particles to form the assembled particles, a different set of process parameters or conditions may be applied to the solution for improved encapsulation, orientation, sweetness, miscibility, final solution stabilization and long-term stability.

Acceptable additional solvents (e.g., solubility enhancing agents) can include, but are not limited to, polar organic solvents, ethyl alcohol, carbon dioxide, and pH and/or osmotic adjusting agents, including citric acid and phosphoric acid. Acceptable additional processing methods can include, but are not limited to, heating, cooling, pressurizing, treatment under vacuum, mixing, high shear homogenization, filtering, and mixture separating techniques. These additional solvents and processes can be applied to the sweetener composition intermittently or continuously and/or serially and in parallel with one another. In addition, they may be repeated as many times as necessary. The additional solvent(s), if used, can in some aspects be removed by industry recognized mixture separation techniques, such as distillation, degassing, precipitation, filtration and physical separation. In certain aspects the solvent(s) can be removed from the solution by stirring at cold or heated temperatures, and with or without the use of reduced pressure.

In some aspects the organic scaffold particles are formed prior to adding solubilized natural, non-nutritive sweetener molecules thereto. In further aspects one or more of the organic scaffold particles or compositional components thereof are added to a solution of solubilized natural, non-nutritive sweetener molecules, and the combined solution is mixed with high shear homogenization to form the assembled particles. In particular aspects it may be beneficial to add one or more of the organic scaffold particles or compositional components thereof, a solution of solubilized natural, non-nutritive sweetener molecules, and an additional solvent while simultaneously subjecting the combined solution to high shear homogenization while also distilling or degassing the additional solvent. In any of these processes, it may be additionally advantageous to rapidly cool the solution at an appropriate time during the processing to accelerate loading of the natural, non-nutritive sweetener molecules onto the organic scaffold particles and/or to temporarily stabilize the loaded particles before a more permanent stabilization method can be performed.

Natural, non-nutritive sweetener molecules not loaded onto organic scaffold particles may remain in solution after loading, and thus it may be desirable to both minimize the amount of excess natural, non-nutritive sweetener molecules added during loading and also to change solution conditions after loading to facilitate precipitation of excess natural, non-nutritive sweetener molecules into its solid form. Alternatively or additionally, it may be beneficial to provide additional particles or substances, such as highly branched agents or excipients, to adsorb or entrap the solid and/or free natural, non-nutritive sweetener molecules in the solution. In some aspects, filtration methods may be used to remove the sweetener solids and/or excipient-entrapped sweetener molecules. In other aspects filtration may also be used to remove any substance that can cloud the solution (if a clear solution is desired).

For some applications the sweetener composition may be in the form of a "dry powder." Such a form may be easier to transport or may provide a form that may be easier to use in certain applications. In such instances the aqueous solution including the organic scaffold particles and the natural, non-nutritive sweetener molecules may be dried by typical industrial drying methods, including but not limited to evaporative (spray drying, drum drying, etc.) and sublimation (lyophilization, atmospheric spray freeze drying, etc.) methods. In such aspects the removal of the water phase will lead to crystallization of the natural, non-nutritive sweetener molecules on the organic scaffold particles, resulting in assembled particles in the form of a dry sweetener composition. In certain aspects it may be desirable to dry the sweetener composition into amorphous particles. In such aspects additives could be added to provide additional structure onto which the assembled particles can reside. Such additives may be particularly desirable if an oil, fatty acid, or triglyceride is used as the organic scaffold particle. In a particular aspect the natural, non-nutritive sweetener molecules provide the surface for the hydrophobic particle compositional component(s) to adsorb on or to be captured within to facilitate the emulsion to reach a stable dry configuration. In a further aspect the sweetener composition is dried along with at least one or more components of a food, beverage, nutritional or pharmaceutical product.

Amphiphilic natural non-nutritive sweeteners have a structure conducive to providing surfactant properties particularly suited to form and stabilize a lipid/surfactant/water emulsion or colloidal suspension. Suitable amphiphilic natural non-nutritive sweetener surfactants include steviol glycosides, such as stevioside, rebaudioside A, rebaudioside B, rebaudioside C, rebaudioside D, rebaudioside E, rebaudioside M, dulcoside, rubusoside, monk fruit extracts, mogrosides, mogroside V, neohesperidin dihydrochalcone and combinations thereof. These sweeteners exhibit amphiphilic properties because the molecules contain both at least one large hydrophilic region comprised of polar sugar molecules and at least one hydrophobic region formed by its organic backbone. These natural sweeteners are not ideal surfactants because of molecular structural limitations, but can be improved and provide sufficient stabilization to an emulsion or suspension. The improvement requires proper selection of a lipid or lipids that are appropriately miscible with the hydrophobic region of the sweetener. This miscibility improves the orientation of the sweetener molecules on the surface of the particles enhancing their surfactant properties and the overall organoleptic properties of the solution compared to a simple aqueous solution of the sweetener molecules alone.

The surfactant properties of the natural non-nutritional sweeteners affect the formation of the desired emulsion or suspension sweetener particle, including optimizing their size, shape and stability. Through the successful embedding of the sweetener's hydrophobic region in the lipid particle and allowing its hydrophilic region to radiate from the particles' surface, enhanced organoleptic properties of the natural non-nutritive sweetener are expressed when contained in and consumed in food, beverages, nutritional or pharmaceutical products.

To function most appropriately as a surfactant, the amphiphilic regions of the sweetener molecule need to be as chemically and physically compatible as possible with both phases of the emulsion/suspension solution. The polar sugar moieties of the sweetener are generally hydrophilic and, consequently, are soluble in water and in balance with the aqueous portion of the emulsion/suspension solution. Balancing the hydrophobic region of the surfactant sweetener to a lipid particle is more complicated. Commercially available natural, non-nutritive sweeteners usually have their hydrophobic moiety spaced between two hydrophilic regions. Therefore sufficiently embedding (anchoring) the hydrophobic region of the sweetener in the surface of the lipid particles for proper sweetener orientation generally requires molecular bending of the sweetener molecule and/or embedding a larger portion of the molecule than just the hydrophobic region. A bent molecule may require stronger or deeper anchorage to the particle and if the embedded portion of the molecule includes more than the hydrophobic region, then the embedded portion will have an additional polar influence and may not properly anchor. In either or both cases, establishing and maintaining the desired lipid particle/sweetener orientation and attachment requires in some aspects the particle to be sufficiently miscible with the docking region of the sweetener molecule to allow for it to embed to an appropriate depth in the particle. This necessitates at least the surface of the lipid scaffold particles to possess similar solubility properties to the particle docking region of the sweetener molecule.

Various combinations of elements of this disclosure are encompassed by this disclosure, e.g., combinations of elements from dependent claims that depend upon the same independent claim.

Aspects of the Disclosure

In various aspects, the present disclosure pertains to and includes at least the following aspects.

Aspect 1. A lipid-in-water composition, comprising:
a. natural, non-nutritive sweetener molecules;
b. a continuous aqueous phase; and
c. a discontinuous lipid phase comprising a C6-C10 medium chain glyceride,
wherein the composition comprises a total lipid content, and the C6-C10 medium chain glyceride comprises at least 20 wt % of the total lipid content.

Aspect 2. The lipid-in-water composition according to Aspect 1, wherein the natural, non-nutritive sweetener molecules comprise stevioside, rebaudioside A, rebaudioside B, rebaudioside C, rebaudioside D, rebaudioside E, rebaudioside M, dulcoside, rubusoside, monk fruit extracts, mogrosides, neohesperidin dihydrochalcone or a combination thereof.

Aspect 3. The lipid-in-water composition according to Aspect 1 or 2, wherein the natural, non-nutritive sweetener molecule comprises rebaudioside A, mogroside V, or a combination thereof.

Aspect 4. The lipid-in-water composition according to any of Aspects 1 to 3, wherein
the natural, non-nutritive sweetener molecules comprise hydrophilic moieties and hydrophobic moieties,
the hydrophobic moieties of the natural, non-nutritive sweetener molecules are aligned inward towards a hydrophobic region of the C6-C10 medium chain glyceride, and the hydrophilic moieties of the natural, non-nutritive sweetener molecules are aligned outward from the C6-C10 medium chain glyceride.

Aspect 5. The lipid-in-water composition according to any of Aspects 1 to 4, wherein the discontinuous lipid phase further comprises at least one additional component, and the C6-C10 medium chain glyceride is applied to the at least one additional component as a coating.

Aspect 6. The lipid in-water composition according to any of Aspects 1 to 5, wherein the discontinuous lipid phase comprises a matrix or a solid and the natural, non-nutritive sweetener molecules are at least partially physically entrapped within the matrix or the solid.

Aspect 7. The lipid-in-water composition according to any of Aspects 1 to 6, wherein the discontinuous lipid phase further comprises at least one additional component selected from the group consisting of: unsaturated or saturated plant or animal-based fats, oils, fatty acids or butters; waxes, amino acids, peptides; oligopeptides; proteins; protein hydrolysates; carbohydrates; polysaccharides; alginates; natural or synthetic polymers; and any combination thereof.

Aspect 8. The lipid-in-water composition according to any of Aspects 1 to 7, wherein the composition is a suspension or an emulsion.

Aspect 9. The lipid-in-water composition according to Aspect 8, wherein the suspension is a colloidal suspension.

Aspect 10. The lipid-in-water composition according to any of Aspects 1 to 9, wherein the C6-C10 medium chain glyceride comprises at least one of a caproic, caprylic, or capric medium chain triglyceride.

Aspect 11. The lipid-in-water composition according to any of Aspects 1 to 10, wherein the C6-C10 medium chain glyceride is derived from coconut oil.

Aspect 12. The lipid-in-water composition according to any of Aspects 1 to 11, wherein the discontinuous lipid phase comprises at least one additional component selected from the group consisting of coconut oil extracts; sunflower oil; canola oil; soybean oil; vegetable oil; avocado oil; safflower oil; grapeseed oil; hazelnut oil; almond oil; cashew oil; nut oil; castor oil; glycerol monostearate; palm oil; monoglycerides, diglycerides, triglycerides, unsaturated or saturated plant or animal-based fats, oils, fatty acids or butters; amino acids, peptides; oligopeptides; proteins; protein hydrolysates; carbohydrates; polysaccharides; waxes; alginates; natural or synthetic polymers; and any combination thereof.

Aspect 13. The lipid-in-water composition according to any of Aspects 1 to 12, wherein the discontinuous lipid phase comprises at least one additional component selected from the group consisting of edible essential oils; flavor-based oils, including orange oil, lemon oil, lime oil, cinnamon oil and vanilla oil; flaxseed oil; olive oil; rapeseed oil; omega 3 oil; omega 6 oil; omega 9 oil; fish oils; krill oils; long chain oils, fats, fatty acids, monoglycerides, diglycerides, or triglycerides; and any combination thereof.

Aspect 14. The lipid-in-water composition according to any of Aspects 1 to 13, further comprising one or more additional additives.

Aspect 15. The lipid-in-water composition according to Aspect 14, wherein the one or more additional additives comprises a surfactant, a stabilizer, an emulsifier, a hydrocolloidal material such as a gum, a ripening inhibitor, carbonation, a weighting agent, an excipient, a flavoring agent, a coloring agent, a preservative, a masking agent, a texture enhancer, or a combination thereof.

Aspect 16. The lipid-in-water composition according to Aspect 14 or 15, wherein the one or more additional additives is derived from a natural source.

Aspect 17. The lipid-in-water composition according to Aspect 16, wherein the composition comprises an emulsion or a suspension, and the emulsion or the suspension comprises a stability enhancer.

Aspect 18. The lipid-in-water composition according Aspect 17, wherein the natural, non-nutritive sweetener molecules comprise a surfactant for the emulsion or for the suspension.

Aspect 19. The lipid-in-water composition according to any of Aspects 1 to 18, wherein the C6-C10 medium chain glyceride comprises from 20 wt % to 100 wt % of the total lipid content, or from 30 wt % to 100 wt % of the total lipid content, or from 40 wt % to 100 wt % of the total lipid content, or from 50 wt % to 100 wt % of the total lipid content, or from 60 wt % to 100 wt % of the total lipid content, or from 70 wt % to 100 wt % of the total lipid content, or from 80 wt % to 100 wt % of the total lipid content, or from 90 wt % to 100 wt % of the total lipid content.

Aspect 19A. The lipid-in-water composition according to any of Aspects 1 to 19, wherein the C6-C10 medium chain glyceride has its surface area substantially populated by the natural, non-nutritive sweetener molecules.

Aspect 20. The lipid-in-water composition according to any of Aspects 1 to 19A, wherein the composition is in a form of a liquid.

Aspect 21. The lipid-in-water composition according to Aspect 20, wherein the liquid comprises a solubility enhancer.

Aspect 22. A solid composition derived from the lipid-in-water composition according to any of Aspects 1 to 19A.

Aspect 23. The solid composition according to Aspect 22, wherein the solid comprises a dry powder.

Aspect 24. A food, nutritional or pharmaceutical product comprising the sweetener composition or the solid composition according to any of Aspects 1 to 23.

Aspect 25. The food, nutritional or pharmaceutical product according to Aspect 24, wherein the product comprises a beverage, a baked good, a sauce, a dairy product, a protein shake, a protein bar, a chocolate product, a canned, frozen or processed food, a confection, a candy, a cereal, a functional food, a vitamin or nutritional supplement, an orally administered chewable, a lozenge, a thin film or drinkable pharmaceutical, a concentrated or dried product that may be reconstituted into one of the foregoing products, or a product that may be consumed in a concentrated or solid form.

Aspect 26. The composition according to any of Aspects 1 to 23, wherein the composition is stable within a pH range of about 2.5 to about 9.0.

Aspect 27. The composition or product according to any of Aspects 1 to 26, wherein the composition minimizes activation of bitter receptors in an oral cavity when consumed and provides responsive activation of sweet receptors in the oral cavity.

Aspect 28. The composition or product according to any of Aspects 1 to 27, wherein the composition or product provides a more commercially acceptable organoleptic taste profile as compared to a substantially identical composition or product that does not include at least 20 wt % of the total lipid content of the C6-C10 medium chain glyceride.

Aspect 29. A method for forming a lipid-in water composition comprising a natural, non-nutritive sweetener, a continuous aqueous phase, and a discontinuous lipid phase comprising a C6-C10 medium chain glyceride, the method comprising:

preparing a solution of the natural, non-nutritive sweetener molecules; and combining the sweetener with the continuous phase and the discontinuous lipid phase, wherein the composition comprises a total lipid content, and the C6-C10 medium chain glyceride comprises at least 20 wt % of the total lipid content.

Aspect 30. The method according to Aspect 29, wherein the discontinuous lipid phase is combined with the solution with a high shear homogenizer to form the lipid-in-water composition.

Aspect 31. A sweetener composition comprising a plurality of assembled particles comprising natural, non-nutritive sweetener molecules and organic scaffold particles, wherein:
the natural, non-nutritive sweetener molecules comprise hydrophilic moieties and hydrophobic moieties;
the organic scaffold particles comprise one or more compositional components, at least one of the compositional components comprising a C6-C10 medium chain glyceride;
the composition comprises a total lipid content, and the C6-C10 medium chain glyceride comprises at least 20 wt % of the total lipid content;
the hydrophobic moieties of the natural, non-nutritive sweetener molecules are aligned inward towards a hydrophobic region of the one or more compositional components; and
the hydrophilic moieties of the natural, non-nutritive sweetener molecules are aligned outward from the one or more compositional components.

Aspect 32. The sweetener composition according to Aspect 31, wherein the natural, non-nutritive sweetener molecules comprise stevioside, rebaudioside A, rebaudioside B, rebaudioside C, rebaudioside D, rebaudioside E, rebaudioside M, dulcoside, rubusoside, monk fruit extracts, mogrosides, mogrosides, neohesperidin dihydrochalcone, or a combination thereof.

Aspect 33. The sweetener composition according to Aspect 31 or 32, wherein the natural, non-nutritive sweetener molecule comprises rebaudioside A, mogroside V, or a combination thereof.

Aspect 34. The sweetener composition according to any of Aspects 31 to 33, wherein the medium chain glyceride is a medium chain triglyceride.

Aspect 35. The sweetener composition according to any of Aspects 31 to 34, wherein organic scaffold particles further comprise at least one additional compositional component, and the C6-C10 medium chain glyceride is applied to the at least one additional compositional component as a coating.

Aspect 36. The sweetener composition according to any of Aspects 31 to 35, wherein the organic scaffold particles comprise a hydrophobic region.

Aspect 37. The sweetener composition according to Aspect 36, wherein the hydrophobic moieties of the natural, non-nutritive sweetener molecules are aligned inward towards the hydrophobic region of the one or more compositional components of the organic scaffold particles and held in place by hydrophobic/hydrophilic forces.

Aspect 38. The sweetener composition according to Aspect 37, wherein the hydrophobic/hydrophilic forces are van der Waals forces.

Aspect 39. The sweetener composition according to Aspect 37, wherein the hydrophobic/hydrophilic forces are hydrophobic effect aggregation forces.

Aspect 40. The sweetener composition according to Aspect 36, wherein the hydrophobic moieties of the natural, non-nutritive sweetener molecules are aligned inward towards the hydrophobic region of the one or more compositional components of the organic scaffold particles and held in place by hydrogen bonding.

Aspect 41. The sweetener composition according to any of Aspects 31 to 40, wherein the one or more compositional components of the organic scaffold particles comprise a matrix or a solid and the natural, non-nutritive sweetener molecules are at least partially physically entrapped within the matrix or the solid.

Aspect 42. The sweetener composition according to any of Aspects 31 to 41, wherein the organic scaffold particles comprise the C6-C10 medium chain glyceride and at least one or more compositional components selected from the group consisting of: unsaturated or saturated plant or animal-based fats, oils, fatty acids or butters; waxes, amino acids, peptides; oligopeptides; proteins; protein hydrolysates; carbohydrates; polysaccharides; alginates; natural or synthetic polymers; and any combination thereof.

Aspect 43. The sweetener composition according to any of Aspects 31 to 42, wherein the sweetener solution is a suspension or an emulsion and the suspension is optionally a colloidal suspension.

Aspect 44. The sweetener composition according to any of Aspects 31 to 43, wherein the C6-C10 medium chain glyceride comprises at least one of a caproic, caprylic, or capric medium chain triglyceride.

Aspect 45. The sweetener composition according to any of Aspects 31 to 44, wherein the medium chain glyceride is derived from coconut oil.

Aspect 46. The sweetener composition according to any of Aspects 31 to 45, wherein the organic scaffold particles comprise at least one compositional component selected from the group consisting of: coconut oil extracts; sunflower oil; canola oil; soybean oil; vegetable oil; avocado oil; safflower oil; grapeseed oil; hazelnut oil; almond oil; cashew oil; nut oil; castor oil; glycerol monostearate; palm oil; monoglycerides, diglycerides, triglycerides, unsaturated or saturated plant or animal-based fats, oils, fatty acids or butters; amino acids, peptides; oligopeptides; proteins; protein hydrolysates; carbohydrates; polysaccharides; waxes; alginates; natural or synthetic polymers; and any combination thereof.

Aspect 47. The sweetener composition according to any of Aspects 31 to 46, wherein the organic scaffold particles comprise at least one compositional component selected from the group consisting of: edible essential oils; flavor-based oils, including orange oil, lemon oil, lime oil, cinnamon oil and vanilla oil; flaxseed oil; olive oil; rapeseed oil; omega 3 oil; omega 6 oil; omega 9 oil; fish oils; krill oils; long chain oils, fats, fatty acids, monoglycerides, diglycerides, or triglycerides; and any combination thereof.

Aspect 48. The sweetener composition according to any of Aspects 31 to 47, wherein the organic scaffold particles are generally spherical in shape.

Aspect 49. The sweetener composition according to any of Aspects 31 to 48, wherein the organic scaffold particles have a particle size of from about 1 nm to about 10 microns (µm).

Aspect 50. The sweetener composition according to Aspect 49, wherein the organic scaffold particles have a particle size of from about 10 nm to about 1 µm.

Aspect 51. The sweetener composition according to any of Aspects 31 to 50, further comprising one or more additional additives.

Aspect 52. The sweetener composition according to Aspect 51, wherein the one or more additional additives comprises a surfactant, a stabilizer, an emulsifier, a hydrocolloidal material such as a gum, a ripening inhibitor, carbonation, a weighting agent, an excipient, a flavoring agent, a coloring agent, a preservative, a masking agent, a texture enhancer, or a combination thereof.

Aspect 53. The sweetener composition according to Aspect 51 or 52, wherein the one or more additional additives is derived from a natural source.

Aspect 54. The sweetener composition according to any of Aspects 31 to 53, wherein the composition is in a form of an emulsion or a suspension.

Aspect 55. The sweetener composition according to Aspect 54, wherein the emulsion or the suspension comprises a stability enhancer.

Aspect 56. The sweetener composition according Aspect 54 or 55, wherein the natural, non-nutritive sweetener molecules is a surfactant for the emulsion or for the suspension.

Aspect 57. The sweetener composition according to any of Aspects 31 to 56, wherein the composition is in a form of a liquid.

Aspect 58. The sweetener composition according to Aspect 57, wherein the liquid comprises a solubility enhancer.

Aspect 59. The sweetener composition according to any of Aspects 31 to 56, wherein the composition is in a form of a solid.

Aspect 60. The sweetener composition according to Aspect 59, wherein the solid comprises a dry powder.

Aspect 61. The sweetener composition according to any of Aspects 31 to 56, wherein:
the natural, non-nutritive sweetener molecules comprise rebaudioside A;
the C6-C10 medium chain glyceride comprises a C8 medium chain triglyceride;
the organic scaffold particles are generally spherical in shape and have a particle size of from about 1 nm to about 1 μm; and
the sweetener composition is in the form of an emulsion.

Aspect 61A. The sweetener composition according to any of Aspects 31 to 61, wherein the plurality of assembled particles have their surface area substantially populated by the natural, non-nutritive sweetener molecules.

Aspect 62. A food, nutritional or pharmaceutical product comprising the sweetener composition according to any of Aspects 31 to 61A.

Aspect 63. The food, nutritional or pharmaceutical product according to Aspect 62, wherein the product comprises a beverage, a baked good, a sauce, a dairy product, a protein shake, a protein bar, a chocolate product, a canned, frozen or processed food, a confection, a candy, a cereal, a functional food, a vitamin or nutritional supplement, an orally administered chewable, a lozenge, a thin film or drinkable pharmaceutical, a concentrated or dried product that may be reconstituted into one of the foregoing products, or a product that may be consumed in a concentrated or solid form.

Aspect 64. The sweetener composition according to any of Aspects 31 to 63, wherein each of the assembled particles comprises a surface area, and a sufficient number of the hydrophobic moieties of the natural, non-nutritive sweetener molecules are aligned inward towards the hydrophobic region of the one or more compositional components of the organic scaffold particles so as to substantially populate the surface area of the assembled particle.

Aspect 65. The sweetener composition according to Aspect 64, wherein each of the assembled particles comprises a hydrophilic outer shell.

Aspect 66. The sweetener composition according to any of Aspects 31 to 65, wherein the composition is stable within a pH range of about 2.5 to about 9.0.

Aspect 67. The sweetener composition according to any of Aspects 31 to 66, wherein the composition minimizes activation of bitter receptors in the oral cavity and provides responsive activation of sweet receptors in the oral cavity when consumed.

Aspect 68. The sweetener composition according to any of Aspects 31 to 67, wherein the composition provides a more commercially acceptable organoleptic taste profile as compared to a substantially identical sweetener composition comprising the same natural, non-nutritive sweetener molecules but that does not include at least 20 wt % of the total lipid content of the C6-C10 medium chain glyceride.

Aspect 69. The sweetener composition according to any of Aspects 31 to 68, wherein the C6-C10 medium chain glyceride comprises from 20 wt % to 100 wt % of the total lipid content, or from 30 wt % to 100 wt % of the total lipid content, or from 40 wt % to 100 wt % of the total lipid content, or from 50 wt % to 100 wt % of the total lipid content, or from 60 wt % to 100 wt % of the total lipid content, or from 70 wt % to 100 wt % of the total lipid content, or from 80 wt % to 100 wt % of the total lipid content, or from 90 wt % to 100 wt % of the total lipid content.

Aspect 70. A method for forming a sweetener composition, the sweetener composition comprising assembled particles comprising natural, non-nutritive sweetener molecules comprising hydrophilic moieties and hydrophobic moieties and organic scaffold particles comprising one or more compositional components comprising a C6-C10 medium chain glyceride, the method comprising:
preparing a solution of the natural, non-nutritive sweetener molecules; and
combining the solution with the one or more compositional components of the organic scaffold particles such that the hydrophobic moieties of the natural, non-nutritive sweetener molecules align inward towards a hydrophobic region of the one or more compositional components of the organic scaffold particles and the hydrophilic moieties of the natural, non-nutritive sweetener molecules align outward from the one or more compositional components of the organic scaffold particles,
wherein the composition comprises a total lipid content, and the C6-C10 medium chain glyceride comprises at least 20 wt % of the total lipid content.

Aspect 71. The method according to Aspect 70, wherein the one or more compositional components of the organic scaffold particles are combined with the solution with a high shear homogenizer to form the assembled particles.

Aspect 71A. The method according to Aspect 70 or 71, wherein the assembled particles have their surface area substantially populated by the natural, non-nutritive sweetener molecules.

Aspect 72. A sweetener composition comprising a plurality of assembled particles comprising natural, non-nutritive sweetener molecules and organic scaffold particles comprising a core, wherein
the natural, non-nutritive sweetener molecules comprise hydrophilic moieties and hydrophobic moieties,
the organic scaffold particles comprise one or more compositional components, wherein the one or more compositional components of the organic scaffold particles are selected from the group consisting of: coconut oil extracts; sunflower oil; canola oil; soybean oil; vegetable oil; avocado oil; safflower oil; grapeseed oil; hazelnut oil; almond oil; cashew oil; nut oil; castor oil; monoglycerides, diglycerides, triglycerides, unsaturated or saturated plant or animal-based fats, oils, fatty acids or butters; amino acids; peptides; oligopeptides; proteins; protein hydrolysates; carbohydrates; polysaccharides; natural or synthetic polymers; edible essential oils; flavor-based oils, including orange oil, lemon oil, lime oil, cinnamon oil and vanilla oil; flaxseed oil; olive oil; rapeseed oil; omega 3 oil; omega 6 oil; omega 9 oil; fish oils; krill oils; long chain oils, fats, fatty acids, waxes; alginates and any combination thereof, the hydrophobic moieties of the natural, non-nutritive sweetener molecules are aligned inward towards the core of the organic scaffold particles, the hydrophilic moieties of the natural, non-nutritive sweetener molecules are aligned outward from the organic scaffold particles, and the natural, non-nutritive sweetener molecules are covalently bonded to one or more of the compositional components of the organic scaffold particles.

Aspect 72A. The sweetener composition according to Aspect 72, wherein the plurality of assembled particles have their surface area substantially populated by the natural, non-nutritive sweetener molecules.

Aspect 73. A sweetener composition comprising a plurality of assembled particles comprising natural, non-nutritive sweetener molecules and organic scaffold particles, wherein the natural, non-nutritive sweetener molecules comprise hydrophilic moieties and hydrophobic moieties, the organic scaffold particles comprise at least one compositional component comprising a C6-C10 medium chain glyceride, and the composition comprises a total lipid content, and the C6-C10 medium chain glyceride comprises at least 20 wt % of the total lipid content.

Aspect 74. The sweetener composition according to Aspect 73, wherein the natural, non-nutritive sweetener molecules comprise stevioside, rebaudioside A, rebaudioside B, rebaudioside C, rebaudioside D, rebaudioside E, rebaudioside M, dulcoside, rubusoside, monk fruit extracts, mogrosides, mongroside V, neohesperidin dihydrochalcone or a combination thereof.

Aspect 75. The sweetener composition according to Aspects 73 or 74, wherein the hydrophobic moieties of the natural, non-nutritive sweetener molecules are aligned inward towards a hydrophobic region of the at least one compositional component of the organic scaffold particles, and the hydrophilic moieties of the natural, non-nutritive sweetener molecules are aligned outward from the organic scaffold particles.

Aspect 76. The sweetener composition according to any of Aspects 73 to 75, wherein the organic scaffold particles further comprise: unsaturated or saturated plant or animal-based fats, oils, fatty acids or butters; waxes, amino acids, peptides; oligopeptides; proteins; protein hydrolysates; carbohydrates; polysaccharides; alginates; natural or synthetic polymers; coconut oil extracts; sunflower oil; canola oil; soybean oil; vegetable oil; avocado oil; safflower oil; grapeseed oil; hazelnut oil; almond oil; cashew oil; nut oil; castor oil; glycerol monostearate; palm oil; edible essential oils; flavor-based oils, including orange oil, lemon oil, lime oil, cinnamon oil and vanilla oil; flaxseed oil; olive oil; rapeseed oil; omega 3 oil; omega 6 oil; omega 9 oil; fish oils; krill oils; short chain oils, long chain oils, monoglycerides, diglycerides, or triglycerides; or any combination thereof.

Aspect 77. The sweetener composition according to any of Aspects 73 to 76, wherein the C6-C10 medium chain glyceride comprises at least one of a caproic, caprylic, or capric medium chain triglyceride.

Aspect 78. The sweetener composition according to any of Aspects 73 to 77, wherein organic scaffold particles further comprise at least one additional compositional component, and the C6-C10 medium chain glyceride is applied to the at least one additional compositional component as a coating.

Aspect 79. The sweetener composition according to any of Aspects 73 to 78, wherein the at least one compositional component comprises a matrix and the natural, non-nutritive sweetener molecules are at least partially physically entrapped within the matrix.

Aspect 80. The sweetener composition according to any of Aspects 73 to 79, further comprising one or more additional additives, wherein the one or more additional additives comprises a surfactant, a stabilizer, an emulsifier, a hydrocolloidal material such as gum, a ripening inhibitor, carbonation, a weighting agent, an excipient, a flavoring agent, a coloring agent, a preservative, a masking agent, a texture enhancer, or a combination thereof.

Aspect 81. The sweetener composition according to any of Aspects 73 to 80, wherein the composition is in a form of an emulsion or a suspension.

Aspect 82. The sweetener composition according Aspect 81, wherein the natural, non-nutritive sweetener molecules are a surfactant for the emulsion or for the suspension.

Aspect 83. The sweetener composition according to any of Aspects 73 to 82, wherein each of the assembled particles comprise a hydrophilic outer shell.

Aspect 84. The sweetener composition according to any of Aspects 73 to 83, wherein the composition is in a form of a liquid, solid or dry powder.

Aspect 85. The sweetener composition according to any of Aspects 73 to 84, wherein:

the natural, non-nutritive sweetener molecules comprise rebaudioside A;

the C6-C10 medium chain glyceride is a C8 medium chain triglyceride;

the organic scaffold particles are generally spherical in shape and have a particle size of from about 1 nm to about 1 μm; and the sweetener composition is in a form of an emulsion.

Aspect 86. A food, nutritional or pharmaceutical product comprising the sweetener composition according to any of Aspects 73 to 85.

Aspect 87. The food, nutritional or pharmaceutical product according to Aspect 86, wherein the product comprises a beverage, a baked good, a sauce, a dairy product, a protein shake, a protein bar, a chocolate product, a canned, frozen or processed food, a confection, a candy, a cereal, a functional food, a vitamin or nutritional supplement, an orally administered chewable, a lozenge, a thin film or drinkable pharmaceutical, a concentrated or dried product that may be reconstituted into one of the foregoing products, or a product that may be consumed in a concentrated or solid form.

Aspect 88. The sweetener composition according to any of Aspects 73 to 87, wherein the composition minimizes activation of bitter receptors in an oral cavity when consumed and provides responsive activation of sweet receptors in the oral cavity.

Aspect 89. The sweetener composition according to any of Aspects 73 to 88, wherein the composition provides a more commercially acceptable organoleptic taste profile as compared to a substantially identical sweetener composition comprising the same natural, non-nutritive sweetener molecules but that does not include at least 20 wt % of the total lipid content of the C6-C10 medium chain glyceride.

Aspect 90. The sweetener composition according to any of Aspects 73 to 89, wherein the C6-C10 medium chain glyceride comprises from 20 wt % to 100 wt % of the total lipid content, or from 30 wt % to 100 wt % of the total lipid content, or from 40 wt % to 100 wt % of the total lipid content, or from 50 wt % to 100 wt % of the total lipid content, or from 60 wt % to 100 wt % of the total lipid content, or from 70 wt % to 100 wt % of the total lipid content, or from 80 wt % to 100 wt % of the total lipid content, or from 90 wt % to 100 wt % of the total lipid content.

Aspect 90A. The sweetener composition according to any of Aspects 73 to 90, wherein the plurality of assembled particles have their surface area substantially populated by the natural, non-nutritive sweetener molecules.

Aspect 91. A method for forming a sweetener composition, the sweetener composition comprising a plurality of assembled particles comprising natural, non-nutritive sweetener molecules comprising hydrophilic moieties and hydrophobic moieties and organic scaffold particles comprising at least one compositional component comprising a C6-C10 medium chain glyceride, the method comprising:
    preparing a solution of the natural, non-nutritive sweetener molecules; and
    combining the solution with the at least one compositional component such that the hydrophobic moieties of the natural, non-nutritive sweetener molecules align inward towards a hydrophobic region of the at least one compositional component and the hydrophilic moieties of the natural, non-nutritive sweetener molecules align outward from the at least one compositional component,
    wherein the composition comprises a total lipid content, and the C6-C10 medium chain glyceride comprises at least 20 wt % of the total lipid content.

Aspect 92. The method according to Aspect 91, wherein the at least one compositional component is combined with the solution with a high shear homogenizer to form the plurality of assembled particles.

Aspect 92A. The sweetener composition according to Aspect 91 or 92, wherein the plurality of assembled particles have their surface area substantially populated by the natural, non-nutritive sweetener molecules.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Miscibility (or partition) experiments were conducted using Rebaudioside A (Reb A) as a prototypical amphiphilic natural non-nutritive sweetener and thirteen common food grade oils to determine which oil composition would best support miscibility between the oil and the docking region of the Reb A molecule. For this experiment, the steviol molecule was used to approximate the particle docking region of Reb A. The thirteen common food grade oils were chosen because of their commercial availability and because it is believed they might be acceptable as an additive to a sweetener formulation. The tested oils were Safflower oil, Grapeseed oil, Canola oil, Flaxseed oil, Sunflower oil, Olive oil, Hazelnut oil, Sesame oil, Soybean oil, Room Temperature Liquid Coconut oil and three mixtures of Medium Chain Triglycerides. Most of these oils are mixtures of different chain length constituent oils, as listed below. From this experiment it was found that the oil with the shortest carbon chains (MCT's) and higher purity were the most miscible with steviol, followed by oils containing constituent oils with slightly longer chains (C10, C12, C14) and then oils composed of C18 constituent oils, where the C18 oils with a greater number of double bonds (alpha linolenic, linoleic) were more miscible than C18 oil with a single double bond (oleic). Results are shown in Table 1:

TABLE 1

Miscibility of Reb A in Oils

| Tested Oils | [Steviol]oil/ [Steviol]aqueous | Major Constituent Oil(s) |
|---|---|---|
| MCT C8 | 1.74 | Caprylic |
| MCT C8, C10, C12 | 1.56 | 38% Caprylic, 31% Capric, 31% Lauric |
| MCT C8, C10 | 1.25 | 70% Caprylic, 30% Capric |
| RT Liquid Coconut | 1.42 | High MCT composition |
| Flaxseed | 0.61 | Linoleic, Oleic, Alpha-Linolenic |
| Sunflower | 0.58 | Linoleic, Oleic |
| Sesame | 0.45 | Linoleic, Oleic, Palmitic |
| Soybean | 0.44 | Linoleic, Oleic, Palmitic |
| Safflower | 0.42 | Linoleic, Oleic |
| Canola | 0.41 | Linoleic, Oleic, Alpha-Linolenic |
| Grapeseed | 0.36 | Linoleic, Oleic |
| Hazelnut | 0.30 | Linoleic, Oleic |
| Olive | 0.27 | Linoleic, Oleic, Palmitic |

From published partition coefficients for steviol, cucurbitacin (an approximate representation of the hydrophobic region of mogrosides), MCT oils and the major constituent oils of the other tested oils, it was reaffirmed that steviol has a partition coefficient more closely aligned with the MCT oils (especially C8:0 and C10:0) than with the constituent oils of other tested oils. Partition coefficient data is shown in Table 2:

TABLE 2

Partition Coefficients of Sweetener and Oils

| | Partition Coefficient (log P) |
|---|---|
| Sweetener Compound | |
| Steviol | 3.18 |
| Cucurbitacin | 3.19 |
| Oil/Lipid | |
| MCT Caprylic C8:0 | 2.92 |
| MCT Capric C10:0 | 3.93 |
| MCT Lauric C12:0 | 5.13 |
| Alpha-Linolenic C18:3 | 6.59 |
| Linoleic C18:2 | 7.06 |
| Oleic C18:1 | 7.68 |
| Palmitic C16:0 | 7.23 |
| Stearic C18:0 | 8.02 |

The results of the experiment, supplemented with the published partition coefficient data, support that the steviol and cucurbitacin molecules, which closely approximate the hydrophobic region of natural non-nutritive sweeteners, is most miscible in MCT oils, among the oils tested. Therefore it is believed to best embed and anchor the hydrophobic portion of natural non-nutritive sweeteners in a lipid emulsion or suspension scaffold particle, a medium chain glyceride and in particular aspects an MCT should be utilized or at least be one of the compositional components. It is believed the MCT oils are more miscible with steviol and cucurbitacin, and thus the docking region of natural non-nutritive sweeteners because their shorter chain lengths render them more polar soluble than the longer chain oils.

Figure 7A:
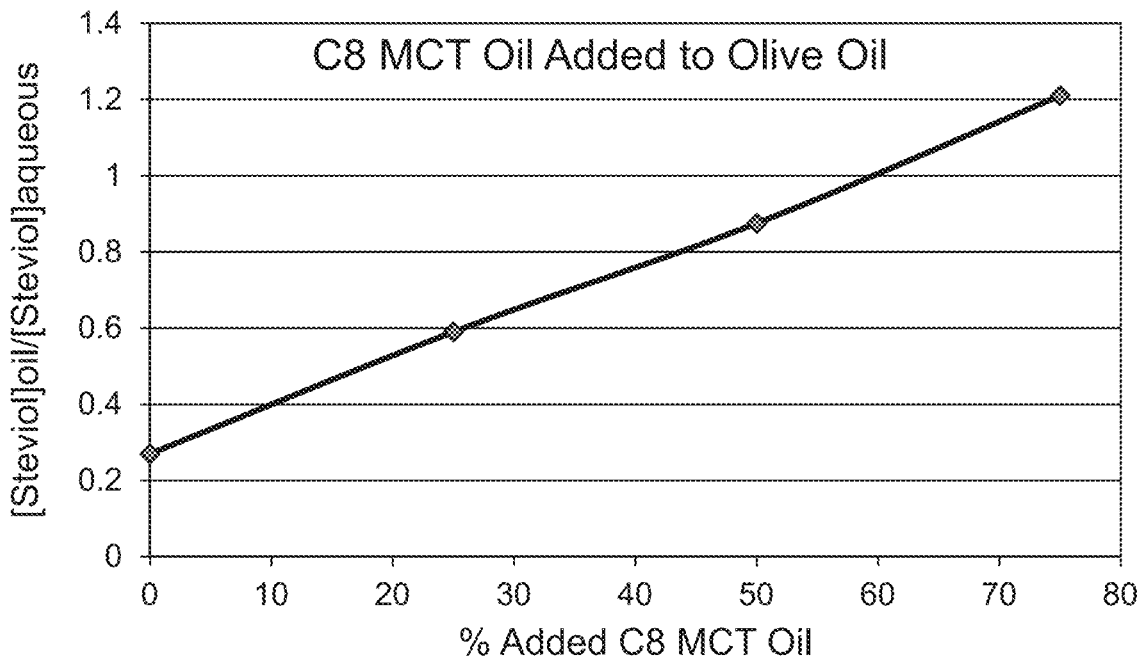
FIGS. 7A and 7B are graphs showing the results of partition studies for various amounts of C8 medium chain triglycerides added to olive oil (FIG. 7A) and flaxseed oil (FIG. 7B).
Figure 7B:
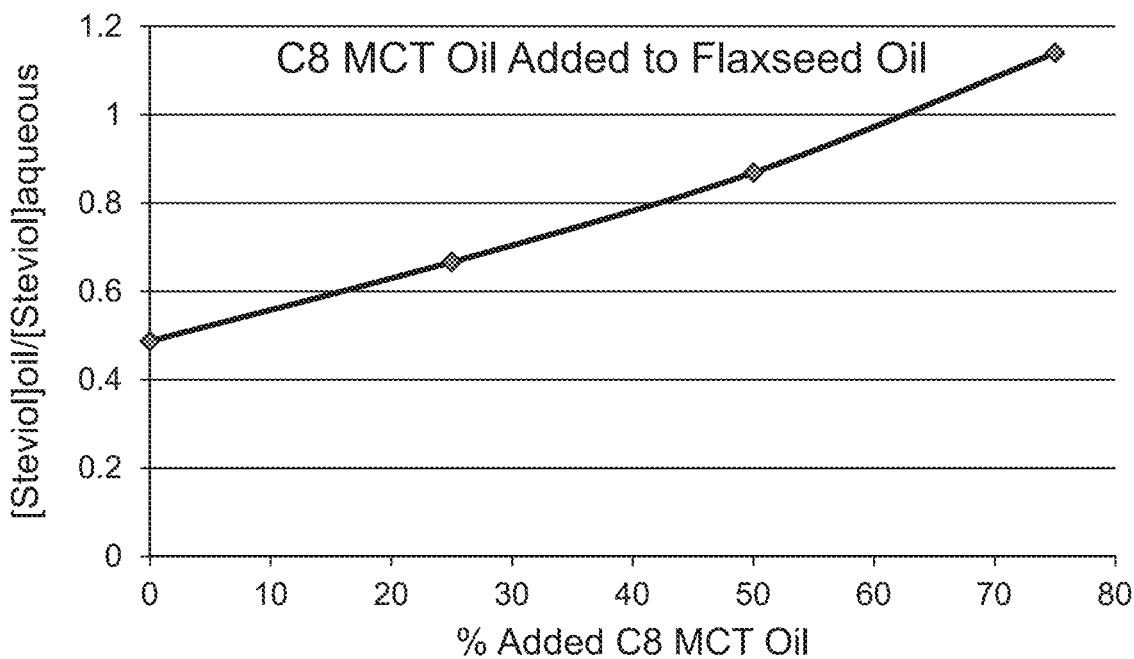

It is further believed the oils with more polar character will migrate towards the surface of particles composed of a mixture of oils or lipids. Thus if a MCT oil is a constituent of, or added to, another oil or lipid, or a mixture of oils or lipids, in a sufficient amount during the formation of the scaffold particles, the MCT oil will migrate to the particle's surface and enhance the embedding of the hydrophobic region of a natural non-nutritive sweetener to that particle. Therefore, MCT oils can be added to other oils, lipids, butters, proteins, etc. to enhance their ability to embed and orient natural non-nutritive sweeteners in the desired configuration for enhanced organoleptic properties. To confirm this effect, additional partition studies were conducted with steviol and olive and flaxseed oils. Four concentrations (0%, 25%, 50% and 75%) of pure MCT C8 oil were added to olive oil (a poor steviol-miscible oil) and flaxseed oil (a more steviol-miscible oil) and tested for steviol-miscibility. The results of the experiments, illustrated graphically in FIG. 7A (olive oil) and FIG. 7B (flaxseed oil) show that a less steviol-miscible, longer chained oil can be rendered more steviol-miscible and thus better able to support the desired configuration of a natural non-nutritive sweetener within an emulsion or suspension by the addition of MCT oil. Extrapolating from the experiments and depending on the starting oil, MCT enhancement of the oil can start yielding improved sweetener orientation benefits with as little as 20% of added MCT oil.

Figure 8:
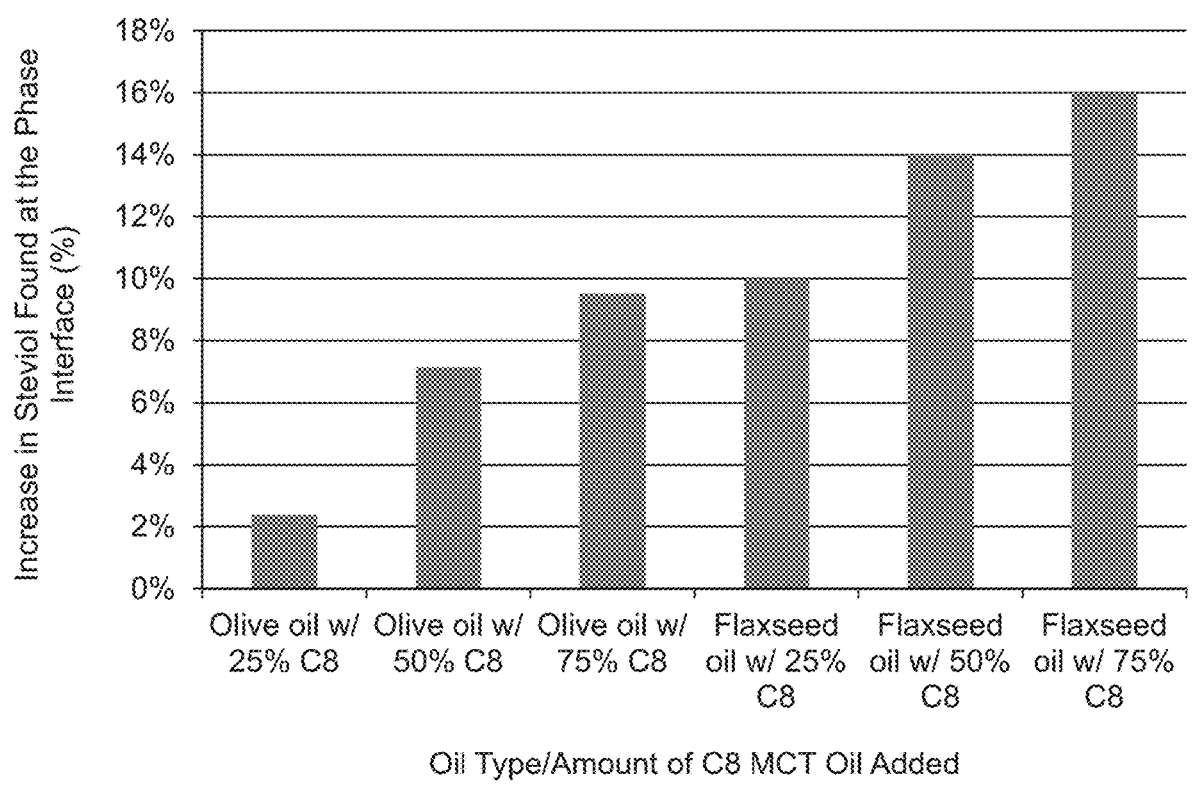
FIG. 8 is a graph illustrating the improvement in miscibility of steviol in olive and flaxseed oils with the addition of various amounts of C8 medium chain triglycerides.

As discussed herein, the sweetness formulation improvement of natural non-nutritive sweeteners may be accomplished in some aspects by the orientation of the sweetener at the interface of lipid particles and its surrounding aqueous phase. Increasing the miscibility between the composition of the lipid particle and steviol, representing the docking (hydrophobic) region of amphiphilic sweeteners, both improves the sweeteners' attachment and orientation at the interface and increases the number of sweetener molecules at the interface. Illustrated in FIG. 8 is a graph showing that by adding increasing percentages of pure C8 medium chain triglycerides to both olive and flaxseed oils, a representative increase in steviol molecules at the interface occurs. This trend mirrors the increased miscibility trend described above.

In addition to allowing the medium chain glyceride (e.g., MCT) oil to migrate to the surface of scaffold particles, the oil can also be externally applied to the surface of particles through methods such as coating or spraying. Applications for enhancing scaffold particle construction with the addition of MCT include: coating or incorporating the desired natural non-nutritive sweetener configuration on or within a much wider range of liquid or solid oils, butters, waxes, proteins, carbohydrates, alginates, peptides, polymers, etc. These compositions would not typically be able to support the desired natural non-nutritive sweetener configuration required for enhanced organoleptic properties.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

That which is claimed is:

1. A sweetener composition comprising a plurality of assembled particles comprising natural, non-nutritive sweetener molecules, organic scaffold particles and at least one additive, wherein
the natural, non-nutritive sweetener molecules comprise hydrophilic moieties and hydrophobic moieties,
the organic scaffold particles comprise at least one compositional component comprising a lipid, and
the at least one additive comprises a surfactant, a stabilizer, an emulsifier, a hydrocolloidal material, a ripening inhibitor, a weighting agent, an excipient, a flavoring agent, a coloring agent, a preservative, a masking agent, a texture enhancer, or a combination thereof.

2. The sweetener composition according to claim 1, wherein the lipid comprises: unsaturated or saturated plant or animal-based fats, oils, fatty acids or butters; waxes; natural or synthetic polymers; coconut oil extracts; glycerol monostearate; edible essential oils; flavor-based oils; omega 3 oil; omega 6 oil; omega 9 oil; fish oils; krill oils; short chain oils, long chain oils, monoglycerides, diglycerides, or triglycerides; or any combination thereof.

3. The sweetener composition according to claim 1, wherein the natural, non-nutritive sweetener molecules comprise stevioside, rebaudioside A, rebaudioside B, rebaudioside C, rebaudioside D, rebaudioside E, rebaudioside M, dulcoside, rubusoside, monk fruit extracts, mogrosides, neohesperidin dihydrochalcone or a combination thereof.

4. The sweetener composition according to claim 1, wherein
the hydrophobic moieties of the natural, non-nutritive sweetener molecules are aligned inward towards a hydrophobic region of the at least one compositional component of the organic scaffold particles, and
the hydrophilic moieties of the natural, non-nutritive sweetener molecules are aligned outward from the organic scaffold particles.

5. The sweetener composition according to claim 1, wherein the organic scaffold particles further comprise: unsaturated or saturated plant or animal-based fats, oils, fatty acids or butters; waxes, amino acids, peptides; oligopeptides; proteins; protein hydrolysates; carbohydrates; polysaccharides; alginates; natural or synthetic polymers; coconut oil extracts; glycerol monostearate; edible essential oils; flavor-based oils; omega 3 oil; omega 6 oil; omega 9 oil; fish oils; krill oils; short chain oils, long chain oils, monoglycerides, diglycerides, or triglycerides; or any combination thereof.

6. The sweetener composition according to claim 5, wherein the at least one compositional component comprises a matrix and the natural, non-nutritive sweetener molecules are at least partially physically entrapped within the matrix.

7. The sweetener composition according to claim 1, wherein the composition is in a form of an emulsion or a suspension.

8. The sweetener composition according to claim 7, wherein the natural, non-nutritive sweetener molecules stabilize the emulsion or the suspension.

9. The sweetener composition according to claim 1, wherein each of the assembled particles comprise a hydrophilic outer shell.

10. The sweetener composition according to claim 1, wherein the composition is in a form of a liquid, solid or dry powder.

11. The sweetener composition according to claim 1, wherein:
the natural, non-nutritive sweetener molecules comprise rebaudioside A;
the organic scaffold particles are generally spherical in shape and have a particle size of from about 1 nm to about 1 µm; and
the sweetener composition is in a form of an emulsion.

12. A food, nutritional or pharmaceutical product comprising the sweetener composition according to claim 1.

13. The food, nutritional or pharmaceutical product according to claim 12, wherein the product comprises a beverage, a baked good, a sauce, a dairy product, a protein shake, a protein bar, a chocolate product, a canned, frozen or processed food, a confection, a candy, a cereal, a functional food, a vitamin or nutritional supplement, an orally administered chewable, a lozenge, a thin film or drinkable pharmaceutical, a concentrated or dried product that may be reconstituted into one of the foregoing products, or a product that may be consumed in a concentrated or solid form.

14. The sweetener composition according to claim 1, wherein the composition minimizes activation of bitter receptors in an oral cavity when consumed and provides responsive activation of sweet receptors in the oral cavity.

15. A method for forming a sweetener composition, the sweetener composition comprising a plurality of assembled particles comprising natural, non-nutritive sweetener molecules comprising hydrophilic moieties and hydrophobic moieties, organic scaffold particles comprising at least one compositional component comprising a lipid, and at least one additive, the method comprising:
preparing a solution of the natural, non-nutritive sweetener molecules; and
combining the solution with the at least one compositional component and the at least one additive such that the hydrophobic moieties of the natural, non-nutritive sweetener molecules align inward towards a hydrophobic region of the at least one compositional component and the hydrophilic moieties of the natural, non-nutritive sweetener molecules align outward from the at least one compositional component,
wherein the at least one additive comprises a surfactant, a stabilizer, an emulsifier, a hydrocolloidal material, a ripening inhibitor, a weighting agent, an excipient, a flavoring agent, a coloring agent, a preservative, a masking agent, a texture enhancer, or a combination thereof.

16. The method according to claim 15, wherein the lipid comprises: unsaturated or saturated plant or animal-based fats, oils, fatty acids or butters; waxes; natural or synthetic polymers; coconut oil extracts; glycerol monostearate; edible essential oils; flavor-based oils; omega 3 oil; omega 6 oil; omega 9 oil; fish oils; krill oils; short chain oils, long chain oils, monoglycerides, diglycerides, or triglycerides; or any combination thereof.

17. The method according to claim 15, wherein the at least one compositional component is combined with the solution with a high shear homogenizer to form the plurality of assembled particles.

18. The method according to claim 15, further comprising adding an additional solvent to the aqueous solution during the step of preparing the aqueous solution, and wherein the method further comprises removing the additional solvent after the step of combining the solution with the at least one compositional component.

19. The method according to claim 15, wherein the additional solvent comprises a polar organic solvent, ethyl alcohol, or carbon dioxide.

* * * * *